(12) United States Patent
Lau et al.

(10) Patent No.: US 11,944,650 B2
(45) Date of Patent: Apr. 2, 2024

(54) METHOD OF TREATING OR PREVENTING HERNIA FORMATION

(71) Applicant: The Board of Supervisors of Louisiana State University and Agricultural and Mechanical College, Baton Rouge, LA (US)

(72) Inventors: Frank Ho Pak Lau, New Orleans, LA (US); Ian Hodgdon, New Orleans, LA (US); Michael Cook, New Orleans, LA (US)

(73) Assignee: THE BOARD OF SUPERVISORS OF LOUISIANA STATE UNIVERSITY AND AGRICULTURAL AND MECHANICAL COLLEGE, Baton Rouge, LA (US)

( * ) Notice: Subject to any disclaimer, the term of this patent is extended or adjusted under 35 U.S.C. 154(b) by 162 days.

(21) Appl. No.: 16/833,099

(22) Filed: Mar. 27, 2020

(65) Prior Publication Data

US 2020/0330522 A1  Oct. 22, 2020

Related U.S. Application Data

(60) Provisional application No. 62/825,547, filed on Mar. 28, 2019.

(51) Int. Cl.
| | |
|---|---|
| *A61K 35/50* | (2015.01) |
| *A61B 17/00* | (2006.01) |
| *A61F 2/00* | (2006.01) |
| *A61K 9/00* | (2006.01) |
| *A61L 27/24* | (2006.01) |
| *A61L 27/36* | (2006.01) |
| *A61L 31/00* | (2006.01) |
| *A61L 31/16* | (2006.01) |
| *A61P 41/00* | (2006.01) |

(52) U.S. Cl.
CPC ............ *A61K 35/50* (2013.01); *A61F 2/0063* (2013.01); *A61K 9/0024* (2013.01); *A61L 27/24* (2013.01); *A61L 27/362* (2013.01); *A61L 31/005* (2013.01); *A61L 31/16* (2013.01); *A61P 41/00* (2018.01); *A61B 2017/00238* (2013.01); *A61F 2002/0072* (2013.01); *A61F 2220/0016* (2013.01); *A61L 2430/34* (2013.01)

(58) Field of Classification Search
CPC ....... A61K 35/50; A61K 9/0024; A61P 41/00; A61F 2/0063; A61F 2220/0016; A61L 31/005; A61L 31/16; A61L 2430/34; A61B 2017/00238

See application file for complete search history.

(56) References Cited

U.S. PATENT DOCUMENTS

| | | | |
|---|---|---|---|
| 2012/0078378 A1* | 3/2012 | Daniel ................ | A61L 27/3834 623/23.72 |
| 2012/0116424 A1* | 5/2012 | Lee ..................... | A61L 24/0005 606/151 |
| 2013/0230561 A1* | 9/2013 | Daniel ................ | A61L 27/3683 424/400 |
| 2013/0238100 A1 | 9/2013 | Young | |
| 2014/0271776 A1 | 9/2014 | Vines et al. | |
| 2014/0343688 A1 | 11/2014 | Morse et al. | |
| 2018/0280572 A1* | 10/2018 | Daniel .................... | A61P 17/02 |

FOREIGN PATENT DOCUMENTS

WO     2017120371     7/2017

OTHER PUBLICATIONS

Koob et al ("Properties of dehydrated human amnion/chorion composite grafts: Implications for wound repair and soft tissue regeneration," Journal of Biomedical materials Research B: Applied Biomaterials, Aug. 2014 vol. 102 B, Issue 6 (Year: 2014).*

Franz et al ("Transforming Growth Factor b2 Lowers the Incidence of Incisional Hernias," Journal of Surgical Research 97, 109-116 (2001) (Year: 2001).*

Short, Dehydrated Human Amniotic-Chorionic Membrane Sheets Prevent Incisional Hernia Formation, Clinical Congress 2018, Boston, MA, Oct. 21-Oct. 25, 2018.

Lau et al., Incisional Hernia Prevention Using Dehydrated Amniotic Membrane in Rat Model, Journal of the American College of Surgeons, Oct. 2018, https://doi.org/10.1016/j.jamcollsurg.2018.08.048.

Reilly et al., Using Dehydrated Human Amnion/Chorion Membrane Allografts for Acute and Reconstructive Burn Care, Burn Surgery & Research, Annals of Plastic Surgery, vol. 78, Suppl 1, pp. S19-S26 (Feb. 2017).

Sheikh et al., Use of dehydrated human amniotic membrane allografts to promote healing in patients with refractory non healing wounds, Int'l Wound J., 11:711-717 (2014).

Franz, The Biology of Hernia Formation, Surg. Clin. North Am., 88(i): 1-vii (Feb. 2008).

Didomenico et al., Aseptically Processed Placental Membrane Improves Healing of Diabetic Foot Ulcerations: Prospective, Randomized Clinical Trial, Plast. Reconstr. Surg. Global Open, 4:e1095 (Oct. 12, 2016).

(Continued)

*Primary Examiner* — Valarie E Bertoglio
*Assistant Examiner* — Matasha Dhar
(74) *Attorney, Agent, or Firm* — Naira Simmons; Pierson Ferdinand, LLC

(57) ABSTRACT

A method of preventing or reducing the occurrence and/or development of a hernia within a subject at risk of developing a hernia includes implanting a graft material in contact with an opening in an abdominal wall. The graft material promotes healing of the abdominal wall and includes placental or placental derived tissue.

14 Claims, 11 Drawing Sheets
Specification includes a Sequence Listing.

(56) References Cited

OTHER PUBLICATIONS

Koob et al., Biological properties of dehydrated human amnion/chorion composite graft: implications for chronic wound healing, Int. Wound J. 10:493-500 (2013).

Bosanquet et al., Systematic Review and Meta-Regression of Factors Affecting Midline Incisional Hernia Rates: Analysis of 14618 Patients, PLOS One, 10(9):e0138745 (Sep. 21, 2015).

International Search Report and Written Opinion, issued in PCT/US2020/025165, dated Jul. 1, 2020.

"Regulatory Considerations for Human Cells, Tissues, and Cellular and Tissue-Based Products: Minimal Manipulation and Homologous Use", FDA, Jul. 2020.

\* cited by examiner

| Age | Gender | Risk Factors ||||| Hernia Outcomes |||
|---|---|---|---|---|---|---|---|---|---|
| | | | | | | | | | |
| 65 | M | 29 | Yes | 50 pack years | Felty syndrome, Leukemia, Perforated Diverticulitis | Midline abdominal fascia | Extremely High | 0.65 | No | 5 months | Direct visualization (surgical re-exploration) | Is he on chemotherapy? |
| Same patient as above | | | | | | Ostomy defect | Extremely High | 0.65 | No | 5 months | Direct visualization (surgical re-exploration) | |
| 60 | M | 26 | | | Bowel obstruction, cocaine use, h/o ventral hernia | Midline abdominal fascia | High | 0.4 | No | 8 months | CT abdomen | Subsequently underwent nephrectomy by urology and developed a hernia |
| 46 | M | | | | Perforated Diverticulitis | Midline abdominal fascia | High | 0.4 | No | 11 months | Phone call | Patient says he could plank between 2 cars |
| 52 | M | 19 | Yes | | COPD | Midline abdominal fascia | High | 0.4 | No | 2 weeks | Direct visualization (surgical re-exploration) | |
| 92 | M | 16 | | | Emergency Surgery + Perforated colon | Midline abdominal fascia | Extremely High | 0.65 | No | 7 months | Phone call | |
| 30 | M | 23 | | | Emergency surgery | Subcostal incision | High | 0.4 | No | 7 months | Phone call | |
| 30 | M | 24 | | | Ostomy reversal | Ostomy defect | Extremely High | 0.65 | No | 6 months | Physical exam + Phone call | |
| 65 | F | 26 | | | Emergency Surgery + Perforated colon | Ostomy defect | Extremely High | 0.65 | No | 5 months | Direct visualization (surgical re-exploration) | |
| Same patient as above | | | | | | Midline abdominal fascia | High | 0.4 | Yes | 5 months | Direct visualization (surgical re-exploration) | |

Totals 5.25 1
Rate 47.7% 9.1%
Risk Reduction 81.0%

FIG. 4

A
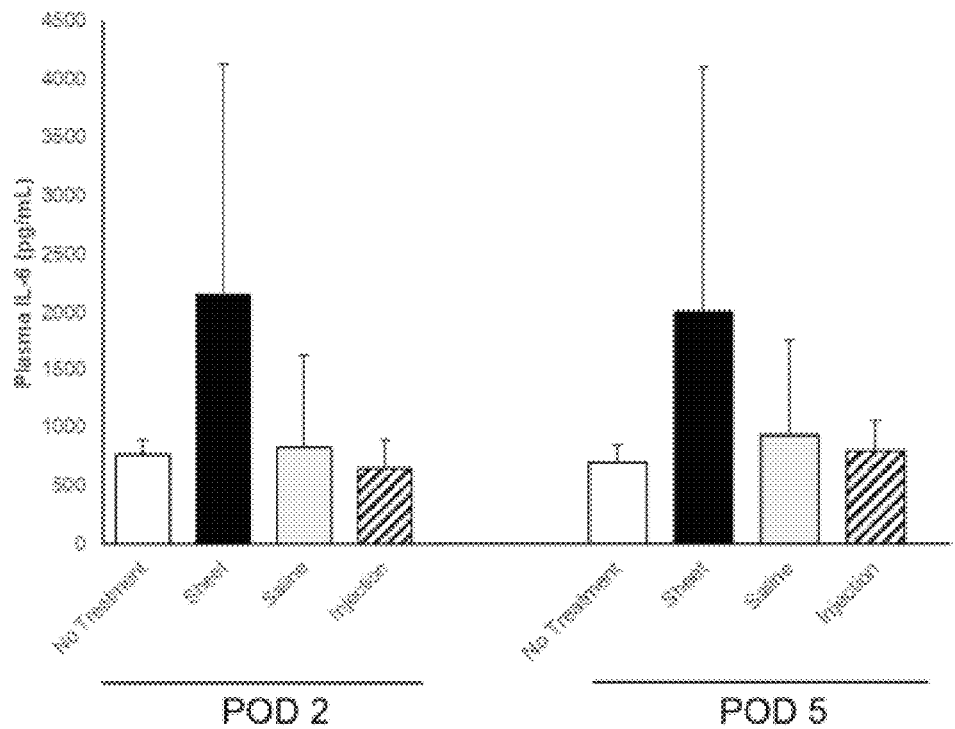
B
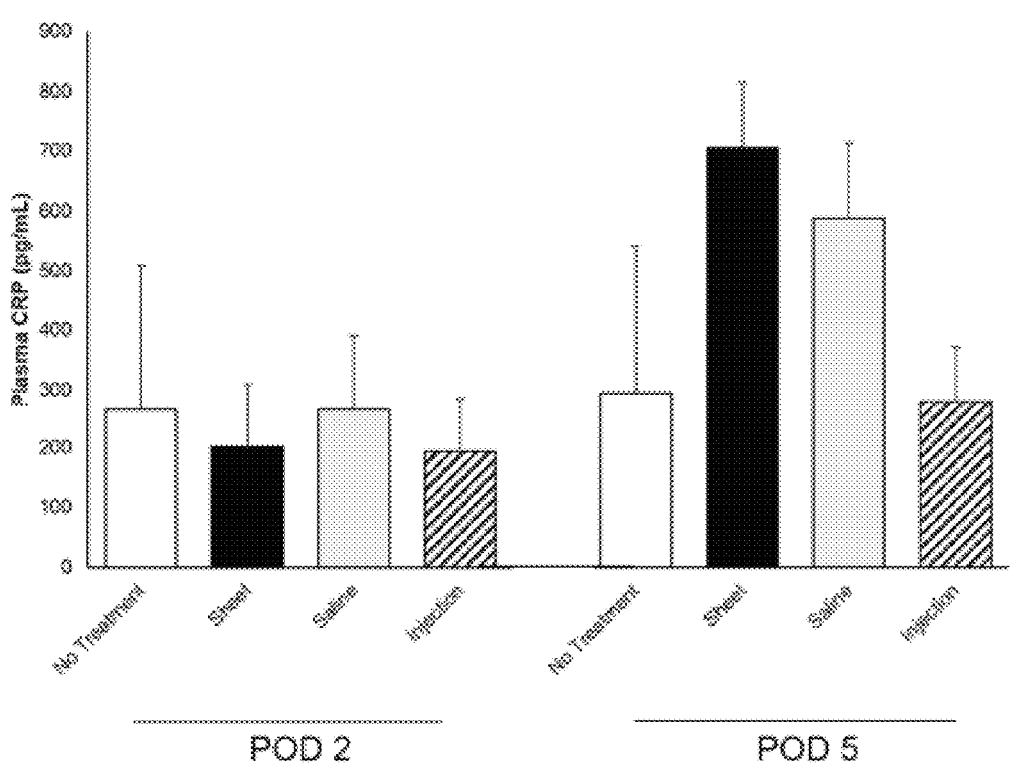
FIG. 9

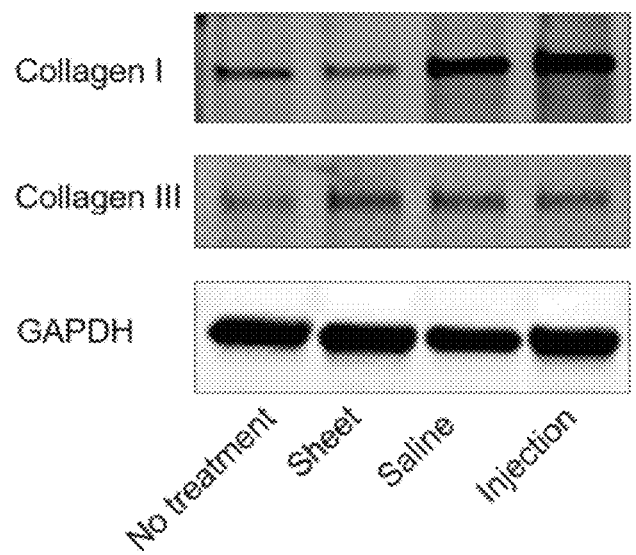
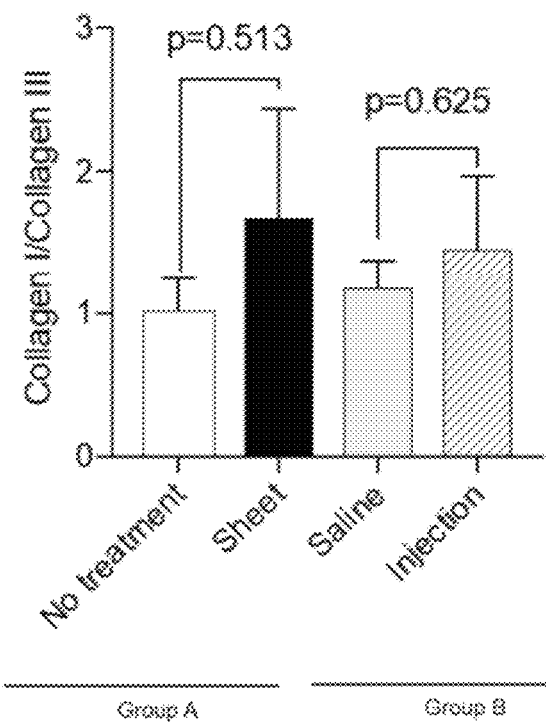
FIG. 10

SEQUENCE LISTING

<160> NUMBER OF SEQ ID NOS: 8

<210> SEQ ID NO 1
<211> LENGTH: 20
<212> TYPE: DNA
<213> ORGANISM: Rattus rattus

<400> SEQUENCE: 1
acttcacaag tcggaggctt                20

<210> SEQ ID NO 2
<211> LENGTH: 20
<212> TYPE: DNA
<213> ORGANISM: Rattus rattus

<400> SEQUENCE: 2
agtgcatcat cgctgttcat                20

<210> SEQ ID NO 3
<211> LENGTH: 23
<212> TYPE: DNA
<213> ORGANISM: Rattus norvegicus

<400> SEQUENCE: 3
ggaacagata cgaagaggaa aca             23

<210> SEQ ID NO 4
<211> LENGTH: 23
<212> TYPE: DNA
<213> ORGANISM: Rattus norvegicus

```
<400> SEQUENCE: 4
tgtttcctct tcgtatctgt tcc                                          23

<210> SEQ ID NO 5
<211> LENGTH: 20
<212> TYPE: DNA
<213> ORGANISM: Rattus rattus

<400> SEQUENCE: 5
tctgcaccct cagcaggttg                                              20

<210> SEQ ID NO 6
<211> LENGTH: 20
<212> TYPE: DNA
<213> ORGANISM: Rattus rattus

<400> SEQUENCE: 6
caacctgctg agggtgcaga                                              20

<210> SEQ ID NO 7
<211> LENGTH: 18
<212> TYPE: DNA
<213> ORGANISM: Rattus rattus

<400> SEQUENCE: 7
agccatgtac gtagccat                                                18

<210> SEQ ID NO 8
<211> LENGTH: 20
<212> TYPE: DNA
<213> ORGANISM: Rattus rattus

<400> SEQUENCE: 8
ctctcagctg tggtggtgaa                                              20
```

METHOD OF TREATING OR PREVENTING HERNIA FORMATION

CROSS-REFERENCE TO RELATED APPLICATIONS

This present application claims priority to and the benefit of U.S. provisional patent application 62/825,547, filed Mar. 28, 2019, the contents of which is hereby incorporated by reference herein.

SEQUENCE LISTING

The instant application contains a Sequence Listing which has been submitted electronically in ASCII format and is hereby incorporated by reference in its entirety. Said ASCII copy, created on May 14, 2020, is named Seq_11971_ST25.txt and is 1629 bytes in size.

TECHNOLOGY FIELD

The present disclosure is directed to methods for preventing development or reducing occurrence of a hernia, more specifically, the present disclosure is related to use of tissue graft material to prevent development or reduce the occurrence of a hernia.

BACKGROUND

Two million laparotomies are performed annually in the United States with incisional hernias (IH) being a major complication. Prevention of IH is an emerging area of research. No standard-of-care has been adopted for prevention of IH. Hernias, such as IH, pose a major burden on the healthcare system, patients, and surgeons. Patients undergoing incisional hernia repair (IHR) risk complications including surgical site infection and hernia recurrence.

SUMMARY

The present disclosure provides methods of preventing or reducing occurrence and/or development of a hernia within a subject at risk of developing a hernia. The method may include selecting a graft material and/or implanting graft material in contact with an opening in the abdominal wall. The graft material may comprise placental tissue. The graft material may promote healing of the abdominal wall opening, thereby preventing or reducing occurrence and/or development of a hernia in the subject. In some embodiments, the graft material may be implanted in a hernia repair procedure to prevent or reduce recurrence of the hernia or development of a hernia recurrence.

The placental tissue may comprise one or more intact sheets, micronized form, powder form, or combination thereof. The placental tissue may include a placental derived tissue. The placental tissue may include processed or unprocessed amnion, chorion, umbilical cord vein, Wharton's jelly, or combinations thereof such as dHACM, cryopreserved umbilical cord and amniotic membrane or membrane matrix, processed and/or unprocessed amniotic membrane and/or chorionic membrane, processed and/or unprocessed umbilical cord, or processed and/or unprocessed umbilical cord and processed and/or unprocessed amniotic membrane and/or chorionic membrane.

In one embodiment, the graft material may be aligned with the opening in the abdominal wall.

In one embodiment, the opening comprises a surgical incision.

In one embodiment, the opening comprises debrided fascia.

In any of the above embodiments or another embodiment, the graft material is configured to promote healing of abdominal fascial edges.

In one embodiment, the graft material may not be actively affixed to the abdominal wall.

In another embodiment, the graft material may be anchored to the abdominal wall, such as by pressure, an adhesive, a clip, a tack, a suture, a staple, or a screw.

In one embodiment, the graft material may be implanted over or ventral to the abdominal wall opening.

In one embodiment, the graft tissue may be implanted under or dorsal to the abdominal wall opening.

In one embodiment, the graft tissue may be injected into and along the fascial edges, either before or after the fascial incision was made.

In any of the above embodiments or another embodiment, the method may further comprise substantially or completely closing the abdominal wall opening prior to implanting the graft material.

In some embodiments, the method may further comprise substantially or completely closing the abdominal wall opening after implanting the graft material.

In one embodiment, the abdominal wall opening may be closed with synthetic mesh or biological mesh.

In one embodiment, the abdominal wall opening comprises a surgical incision. For example, the surgical incision comprises an abdominal fascia incision.

In various embodiments, the abdominal wall opening is caused by surgery. For example, the surgery may comprise a laparotomy (celiotomy), laparoscopy, stoma surgery, or repair of abdominal hernia.

In various embodiments, the hernia may comprise an incisional hernia, ventral hernia, umbilical hernia, epigastric hernia, port site hernia, lumbar hernia, inguinal hernia, diaphragmatic hernia, hiatal hernia, Spigelian hernia, or a parastomal hernia.

In an above or another embodiment, the subject at risk of developing a hernia comprises an overweight or obese subject, a subject afflicted with an infection, a subject who underwent a bowel resection, a subject who underwent colon surgery, a subject being administered corticosteroids, a subject being administered chemotherapy, a subject who smokes, a subject who has chronic obstructive pulmonary disease, a subject who is malnourished, a subject who is of advanced age, a subject with uncontrolled diabetes mellitus, a subject with anemia, a subject with a prior hernia, a subject who is pregnant, a subject who previously had more than 2 children, a subject who has a diminished healing capacity, a subject who previously had an "open abdomen" wherein the abdominal fascia incision was closed with suture on the same day as the incision was made, or any combination thereof. For example, the infection comprises a surgical site infection, intra-abdominal infection, deep infections, or superficial abdominal infection.

In any of the above embodiments or another embodiment, the graft material comprises a mammalian tissue.

In a further embodiment, the mammalian tissue comprises endogenous growth factors.

In any of the above embodiments or another embodiment, the graft material may comprises a placental tissue or derivative thereof. For example, the placental tissue may comprise a placenta-derived tissue, a placenta-derived membrane, or a combination thereof. For example, the placenta-derived tissue comprises amnion, chorion, umbilical cord vein, Wharton's jelly, or any combination thereof. For example, the placenta-derived membrane comprises amnion, chorion, or any combination thereof.

In one embodiment, the graft material comprises human amniotic-chorionic membrane.

In one embodiment, the graft material comprises a dehydrated tissue, decellularized tissue, cross-linked tissue, frozen tissue, cryopreserved tissue, fresh tissue, or any combination thereof.

In one embodiment, the graft material is implanted as a sheet, nanoparticle, powder, or injectable.

In some embodiments, the graft material further comprises a synthetic mesh, biological mesh, or tissue scaffold. For example, the biological mesh comprises a mammalian tissue. For example, the mammalian tissue comprises a dermal matrix, or a urinary bladder matrix. For example, the mammalian tissue scaffold comprises a collagen matrix.

Aspects of the present disclosure are further directed towards a method of promoting healing of an opening in the abdominal wall, comprising: obtaining a graft material; and implanting the graft material in a subject, wherein the graft material is implanted in contact with the opening in the abdominal wall, and wherein the graft material promotes healing of the abdominal wall opening.

Still further, aspects of the present disclosure are directed towards a method of promoting facial healing, comprising: obtaining a graft material; and implanting graft material in a subject, wherein the graft material is implanted approximately to the defective region in the fascia, and wherein the graft material promotes healing of the defect in the fascia.

Aspects of the present disclosure are still further directed towards a method of repairing a hernia, comprising: selecting a graft material; and implanting the graft material in contact with an opening in the abdominal wall, wherein the graft material repairs the abdominal wall opening.

Aspects of the present disclosure are directed towards a method of preventing hernia recurrence, comprising: obtaining a graft material; and implanting the graft material in a subject, wherein the graft material is implanted in contact with an opening in the abdominal wall, and wherein the graft material prevents hernia recurrence.

Other objects and advantages of this present disclosure will become readily apparent from the ensuing description.

BRIEF DESCRIPTION OF THE FIGURES

The novel features of the described embodiments are set forth with particularity in the appended claims. The described embodiments, however, both as to organization and manner of operation, may be best understood by reference to the following description, taken in conjunction with the accompanying drawings in which:

FIG. 4 shows clinical data from human hernia prevention studies.

FIG. 9 shows dHACM treatments did not significantly change plasma levels of IL-6 and CRP on POD 2 and 5. Levels were quantified using ELISA. A) In Group A (No Treatment vs. Sheet), mean plasma levels of IL-6 on POD 2 were No Treatment 765.9+/−130.5 pg/mL vs. Sheet 2147.9+/−1978.9 pg/mL (p=0.069). On POD 5 mean plasma levels were No Treatment 659.0+/−604.7 pg/mL vs. Sheet 1883.4+/−2132.9 pg/mL (p=0.09). In Group B (Saline vs. Injection), mean plasma levels of IL-6 on POD 2 were Saline 825.5+/−789.4 pg/mL vs. Injection 649.8+/−242.5 pg/mL (p=0.29); on POD 5 they were Saline 870.5+/−787.8 pg/mL vs. Injection 750.9+/−615.3 pg/mL (p=0.37). B) In Group A (No Treatment vs. Sheet), mean plasma levels of CRP on POD 2 were No Treatment 264.2+/−245.2 pg/mL vs. Sheet 201.2+/−108.7 pg/mL (p=0.28). On POD 5 mean plasma levels were No Treatment 294.6+/−137.6 pg/mL vs. Sheet 704.4+/−493.4 pg/mL (p=0.069). In Group B (Saline vs. Injection), mean plasma levels of CRP on POD 2 were Saline 265.4+/−126.0 pg/mL vs. Injection 194.9+/−91.1 pg/mL (p=0.13); on POD 5 they were Saline 586.7+/−559.5 pg/mL vs. Injection 280.7+/−217.8 pg/mL (p=0.11).

FIG. 10 shows dHACM treatments did not significantly change fascial scar expression of inflammatory markers at 28 days after celiotomy. Total protein from 0.5×0.5 cm region of scar tissue was isolated and analyzed by immunoblotting. A) Western blots for collagen I, III, and GAPDH. B) Image J was used for quantification. Collagen levels were normalized to GAPDH and Collagen VIII ratio were calculated. In Group A (No Treatment vs. Sheet), mean Collagen VIII ratios were No Treatment 1.02+/−0.23 vs. Sheet 1.67+/−0.77 (p=0.513). In Group B (Saline vs. Injection), mean ratios were Saline 1.18+/−0.19 vs. Injection 1.45+/−0.51 (p=0.625).

DESCRIPTION

Figure 1:
FIG. 1 shows an animal model of laparotomy incision.

Two million laparotomies are performed annually in the United States with incisional hernias (IH) being a major complication. A laparotomy refers to a surgical incision into the abdominal cavity, such as for diagnosis of a disease or condition or in preparation for surgery. The incidence of IH following laparotomy averages 12% but has been shown to reach 73% in high risk populations. This leads to 400,000 new IH per year. These hernias pose a major burden on the healthcare system, patients, and surgeons. IH repair (IHR) costs $6-10 billion per year (Hernia Repair Devices and Consumables). Patients undergoing IHR risk complications including surgical site infection (20-30%) and hernia recurrence (20-30%) (Goodenough C, Ko T C, Kao L S "*Development and Validation of a Risk Stratification Score for Ventral Incisional Hernia after Abdominal Surgery: Hernia Expectation Rates in Intra-Abdominal Surgery* (*The HERNIA Project*)." J Am Coll Surg. 2015 April; 220(4):405-413). Surgeons performing IHR frequently use synthetic mesh, which exposes them to mesh-related malpractice suits.

The pathogenesis of IH is not fully understood. The most commonly cited mechanism is mechanical failure, such as suture rupture. Patients with IH face major complications including bowel obstruction, intestinal ischemia, chronic pain and disability. Repair is thus indicated but even under clean, elective circumstances, repair-related complications are frequent and include hernia recurrence, mesh infection, chronic pain, bowel and intra-abdominal organ injury, restrictive ventilator and abdominal pathologies, and sepsis. When IH repairs are performed emergently, as is required for bowel obstruction or strangulation, the incidence of complications rises further.

Preventing and/or reducing rates of primary IH occurrence is thus a key but under-developed strategy. Thus far, IH prevention has largely focused on optimizing mechanical support for the fascial incision. Accepted surgical guidelines include using non-midline incisions, choosing non-absorbing monofilament suture, closing rectus fascia with a single continuous suture, and maintaining a suture to wound length ratio of 4:1. In high-risk patients, prophylactic underlay synthetic mesh can be used but is not standard of care due to its associated risks. Even when used, such prophylactic underlay mesh strategies do not include use of placental tissues (PT), such as placental derived tissues (PDT).

Prior to our work, no clinically-proven strategies have been identified to reduce IH formation rates.

The present disclosure provides methods to promote fascial healing, prevent or reduce occurrence and/or development of a hernia, or prevent or reduce hernia recurrence or development of a recurrent hernia. In various embodiments, methods may include selecting a graft material, such as one comprising a placental tissue (PT) thereof for implantation in contact with, in close proximity to, or adjacent to an opening in the fascia or abdominal wall. The PT may comprise PDT. In a further or another embodiment, methods may include implanting graft material comprising PT in contact with, in close proximity to, or adjacent to an opening in the fascia or abdominal wall. In various embodiments, such methods using PT, which may include PDT, graft material may be utilized to drastically reduce hernia formation rate and/or extent in individuals, such as individuals at risk of developing a hernia. Embodiments described herein may comprise the use of PT, PDT, membranes, components and medical devices in the prevention or reduction in the occurrence, recurrence, and/or development of hernias, such as incisional and parastomal hernias.

Detailed descriptions of one or more preferred embodiments, examples, and configurations are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in any appropriate manner.

Aspects of the present disclosure are directed towards methods of healing an opening in the fascia, such as an incision or a hernia. The term "fascia" refers to a sheet of fibrous tissue that envelops the body or parts of the body beneath the skin. It also encloses muscles or groups of muscles. In embodiments, an opening or incision in the fascia can be prevented or treated as described herein. For example, the opening can comprise incised fascia, that is tissue of the fascia that has been cut, such as by an incision or electrocautery, and excised fascia, that is tissue of the fascia that has been removed by any means.

Aspects of the present disclosure are also directed towards methods of healing an opening in the abdominal wall, such as an abdominal incision or an abdominal hernia. The abdominal wall represents the boundaries of the abdominal cavity, and is split into the posterior (back), lateral (sides), anterior (front) walls, superior (top or towards the head), and inferior (bottom or towards the pelvis). In human anatomy, the layers of the abdominal wall are (from superficial to deep) skin, subcutaneous tissue; fascia (Camper's fascia and Scarpa's fascia); muscle (external oblique abdominal muscle; internal oblique abdominal muscle; rectus abdominis; transverse abdominal muscle; pyramidalis muscle; transversalis fascia; extraperitoneal fat; and peritoneum. It also includes the linea alba, which runs from the xiphoid process to the pubic symphysis in the midline of the abdomen and is a coalescence of several layers of the abdominal wall. The superior boundary of the abdominal cavity is comprised of the diaphragm. The inferior boundary of the abdominal cavity is comprised of the pelvic floor.

In embodiments, the opening, such as an opening caused by a surgical incision or puncture, can result in a hernia. Hernias can also be congenital, or can occur without being the result of surgery. These include inguinal hernias, sports hernias, and Spigelian hernias, for example.

The term "hernia" can refer to a protrusion of a part or structure through the tissues normally containing it. Hernias are typically named for the area where the protrusion occurs. For example, umbilical hernia is a protrusion of fat or viscera through the abdominal wall at the level of the umbilicus. As another example, an "abdominal hernia" can refer to a protrusion through or into any part of the abdominal wall, such as the case when the intestines extrude through a weakened area in the abdominal wall. The abdominal wall boundaries are the diaphragm superior, pelvis inferior, spine posterior, abdominal wall muscular lateral and anterior. For example, an abdominal wall hernia can refer to a protrusion of abdominal organ or fat protrusion through the boundary.

The most common types of hernias are inguinal (groin), incisional (resulting from an incision), femoral (groin), umbilical (belly button), parastomal, and hiatal/diaphragmatic (upper abdomen). Non-limiting examples of other types of hernias comprise lumbar, diaphragmatic, ventral, postoperative, epigastric, Spigelian, weakness in the pelvic floor (such as obturator hernia), or generally any abdominal wall related hernia. Non-limiting examples of non-incisional hernias comprise inguinal hernias, spigelian hernias, sports hernias, lumbar hernia, femoral hernia, diaphragmatic hernia, hiatal hernia, and/or obturator hernia. The skilled artisan will recognize that in the most general interpretation, a hernia can occur in any hollow body organs and/or said natural and/or said artificial orifices and/or said spaces and/or said post-operative spaces.

For example, embodiments of the present disclosure may be particularly suited for preventing, reducing occurrence or development, and/or treating a parastomal hernia. A parastomal hernia is a type of incisional hernia (IH) that allows protrusion of abdominal contents through the abdominal wall defect created during ostomy formation. Unlike a hernia development in a surgical incision for which the fundamental problem is healing between tissues that have been approximated, ostomy creation introduces an abdominal wall defect for which no healing is expected. A parastomal hernia forms as the defect is continually stretched by the forces tangential to its circumference. This stretching allows additional abdominal viscera to herniate adjacent to the ostomy. The reported incidence of parastomal hernia varies widely and is related to the type of ostomy constructed, the duration of follow-up after ostomy construction, and the definition used to identify parastomal hernia. The incidence of parastomal hernia is reported as ranging from 0 to 50 percent, depending upon the type of ostomy.

Embodiments of the present disclosure are particularly suited for preventing, reducing the occurrence and/or development, and/or treating an incisional hernia (IH). An IH refers to a protrusion of tissue that forms at the site of a surgical incision or healing surgical scar. The term "surgical incision site" can refer to the body or tissue surface to which a surgical incision is to be made or has been made, as well as the immediate area adjacent to or in close proximity to the incision. The "surgical incision site" can be referred to as an "opening" in a tissue. This immediate area extends in all directions beyond the incision. For example, the immediate area can extend by about 2 to 12 inches beyond the incision. For example, the immediate area can extend 2 to 12 inches beyond the incision. For example, an abdominal hernia can result from an incision causing an opening in the abdominal wall, and thus can be referred to as an incisional hernia. Surgeries that can result in IH, for example, comprise laparotomy (celiotomy), laparoscopy, stoma surgery, or repair of abdominal hernia. A hernia can also form from devascularization or weakening of the abdominal wall, such as from the surgery itself or a surgical site infection secondary to the surgery.

Embodiments of the present disclosure can also be suited for treating a hernia and area in proximity to the hernia. For example, the area in proximity to hernia may comprise an abdominal wall musculature and fascia, diaphragm, and/or pelvis.

Although hernias can occur in any subject, particular groups of individuals are especially susceptible to hernia development. In various embodiments, the methodologies described herein may find beneficial application to prevent, reduce occurrence and/or development, and/or treat a hernia in a subject a risk of developing a hernia. For example, subjects at risk of developing a hernia may comprise those who are obese and/or afflicted with diabetes, afflicted with an infection (such as a surgical site infection, intra-abdominal infection, deep tissue infection, or superficial abdominal infection), malnourished, undergoing preoperative chemotherapy, of advanced age, pregnant, afflicted with connective tissue disease, suffering from chronic cough, underwent intraoperative blood transfusion, underwent a surgery (such as a bowel resection, colon surgery, or emergency surgery), are being administered corticosteroids, smokes, has chronic obstructive pulmonary disease, has emphysema, has peripheral vascular disease, has diabetes mellitus Type 1 or Type 2, or any combination thereof. Other risk factors include, but are not limited to, congestive heart failure, renal failure, liver failure (especially with ascites), patients with constipation or BPH (intentional increase in abdominal pressure to void or defecate), patients with upper or lower extremity amputations or weakness (via increased dependence on core musculature). Patients with jobs requiring heavy lifting, or caring for invalid family members can also predispose to hernia formation. According to Mayo clinic, being male and being Caucasian increase your risk for hernia, as well as family history of hernias.

As introduced above, the various embodiments of the present disclosure include administering, e.g., implanting, graft material in a subject to promote fascial healing; prevent and/or reduce hernia occurrence, development, and/or recurrence; and/or prevent the failure of hernia repair. The term "graft material" can refer to a material that can be placed on, attached to or inserted into a bodily part. The graft material can be a tissue graft material which comprises tissue and/or processed tissue. The tissue graft material can further comprise additional compositions, such as synthetics or biological compositions, as described herein.

The graft material can be a mammalian tissue or derivative thereof, such as a PT or PDT. A tissue derivative is prepared from a tissue, such as a mammalian tissue, through physical and/or chemical treating of the natural tissue to produce a derivative tissue that retains the natural structure and/or basic characteristics of the natural tissue. For example, the tissue can be dehydrated, such as chemically dehydrated or freeze-dried; decellularized; cross-linked; frozen; cryopreserved; fresh; decontaminated; cleaned; or any combination thereof, thereby producing a tissue derivative. A tissue derivative may also be prepared from cells isolated from the tissue, such as placental cell-derived exosomes.

In embodiments, the graft material comprises an allograft. The term "allograft" can refer to a tissue graft from a donor of the same species as the recipient but not genetically identical. For example, the allograft can comprise a PT or PDT allograft, such as a dehydrated human amnion-chorion membrane (dHACM) allograft. In other embodiments, the graft material comprises an autograft. The term "autograft" can refer to a graft of tissue from one point to another on the same individual's body.

In embodiments, the graft material can be a placental tissue (PT) graft. See, for example, US Patent Application Publication No. 20130230561A1, which is incorporated herein by reference in its entirety. The term "placental tissue" (PT) can refer to one or more of the individual components of the placenta (but not the entire placenta).

Such components are well known in the art and include, a placental membrane (such as amnion and/or chorion), umbilical cord vein, Wharton's jelly and any combination thereof. Included within the term "amnion" are unmodified and modified amnion. Modified amnion includes amnion in which the epithelial layer has been removed (mechanically, chemically or enzymatically) while retaining the fibroblast cellular layer, amnion which has been completely decellularized as well as amnion which retains the epithelial layer while having the fibroblast layer removed. The term "placental tissue" (PT) can refer to the intact tissue itself, or components of the tissue such as the decellularized matrix, cellularized matrix, exosomes, such as those produced by placental derived stem cells, or the cells themselves.

Graft material comprising PT or "PT graft" refers to one or more layers of placental tissue are suitable for use as a graft in treating a condition in a mammal such as a human. PT grafts can be implanted in their unprocessed form, or alternatively can be processed into a tissue derivative. For example, the PT may be processed to generate PDT in any fashion that preserves the tissue's ability to elute growth factors, or preserves the extracellular matrix in a fashion that promotes healing of fascia. For example, the PT can be dehydrated, such as chemically dehydrated or freeze-dried; decellularized; cross-linked; frozen; cryopreserved; fresh; decontaminated; cleaned; or any combination thereof.

PT, such as PDT, are commercially available in many forms and have been used as healing adjuncts for a broad range of external wounds, such as including diabetic foot wounds (Didomenico L A, Orgill D P, Galiano R D, et al. "*Aseptically Processed Placental Membrane Improves Healing of Diabetic Foot Ulcerations: Prospective, Randomized Clinical Trial.*" Plast Reconstr Surg Glob Open. 2016; 4(10):e1095.; Zelen C M. "*An evaluation of dehydrated human amniotic membrane allografts in patients with DFUs.*" J Wound Care. 2013; 22(7):347-351; Zelen C M, Serena T E, Denoziere G, et al. "*A prospective randomised comparative parallel study of amniotic membrane wound graft in the management of diabetic foot ulcers.*" Int Wound J. 2013b; 10(5):502-507; Zelen C M, Serena T E, Snyder R J. "*A prospective, randomised comparative study of weekly versus biweekly application of dehydrated human amnion/chorion membrane allograft in the management of diabetic foot ulcers.*" Int Wound J. 2014; 11(2):122-128; Zelen C M, Snyder R J, Serena T E, et al. "*The use of human amnion/chorion membrane in the clinical setting for lower extremity repair: a review.*" Clin Podiatr Med Surg. 2015b; 32(1):135-146; Zelen C M, Poka A, Andrews J. "*Prospective, randomized, blinded, comparative study of injectable micronized dehydrated amniotic/chorionic membrane allograft for plantar fasciitis—a feasibility study.*" Foot Ankle Int. 2013a; 34(10):1332-1339), plantar fasciitis (Zelen et. al, 2013a), chronic non-healing wounds (Sheikh E S, Sheikh E S, Fetterolf D E. "*Use of dehydrated human amniotic membrane allografts to promote healing in patients with refractory non healing wounds.*" Int Wound J. 2014; 11(6):711-7), and lower extremity wounds (Zelen et. al, 2015). PT, however, have not previously been used to improve fascial healing, prevent hernia development, or prevent hernia recurrence.

In various embodiments, the PT graft can be a dehydrated human amnion/chorion membrane (dHACM). See, for example, Lei, Jennifer, et al. "*Dehydrated human amnion/chorion membrane (dHACM) allografts as a therapy for orthopedic tissue repair.*" Techniques in Orthopaedics 32.3 (2017): 149-157, which is incorporated by reference herein in its entirety. This PDT elutes over 285 regulatory molecules including platelet-derived growth factor-AA (PDGF-AA), PDGF-BB, transforming growth factor α (TGFα), TGFβ1, basic fibroblast growth factor (bFGF), epidermal growth factor (EGF), placental growth factor (PLGF) and granulocyte colony-stimulating factor (GCSF) and IL-4, 6, 8 and 10, and TIMP 1, 2 and 4. dHACM is a commercially available healing adjunct and is currently available in at least two forms 1) as implantable sheets that elute regulatory proteins post-implantation, yielding sustained delivery of multiple growth factors, and 2) as a micronized injection that can be placed along the fascial incision that similarly elute multiple growth factors over time. Example dHACM products include Amniofix® and Epifix®, manufactured by MiMedx Group Inc., Marietta, GA, USA.

In one embodiment, the PT comprises cryopreserved umbilical cord and amniotic membrane matrix. An example of this PDT is commercially available under the name Neox 100®, Amniox Medical Inc., Miami, FL. A similar cryopreserved umbilical cord and amniotic membrane product, Neox Cord 1K®, also manufacture by Amniox Medical Inc., is also commercially available. In another example embodiment, the PT comprises a tri-layer dehydrated placenta-derived tissue comprised of unseparated amniotic membrane and chorionic membrane with the intact intermediate layer, an example of which is AminoWrap2™, Direct Biologics LLC, St. Louis, MO. Still another example embodiment, the PT comprises dehydrated trilayer amnion and chorion, an example of which is NuShield®, Organogenesis Inc., Canton MA. It is to be appreciated that in various embodiments, the graft material may comprise PT including a combination of native/unprocessed and derived PT. In some embodiments, the graft material may comprise PT including a combination of PDT with or without native/unprocessed PT.

In embodiments, the graft material including PT can be applied to the subject in various forms. For example, the graft material can be applied in membrane form, for example as a sheet or sheet-like. Further, the graft material can be applied in micronized form or powdered form, such as produced when membrane tissue has been cryomilled and sieved for particulate sizing. For example, micronized form grafts can be produced using 180 and 25 μm sieves for particulate sizing. The micronized or powdered graft material can be spread or scattered over an opening, such as an abdominal fascia incision that has been closed with suture. Alternatively, the micronized tissue can be reconstituted in a solution, such as a saline solution, and administered to patients as a flowable or injectable material. For example, the micronized graft material can be solubilized/dissolved and injected within 4-cm of an abdominal fascia incision that has been closed with suture.

As discussed herein, the graft material including PT can be provided as a flat sheet or sheet-like form, such as in membrane form, or as a nanoparticle or powder, which can be referred to as micronized form. The terms "sheet" and "sheet-like," as used herein, generally refer to a broad, relatively thin, surface or layer of a material. Such sheets can, but may not, be relatively flexible, and may be flat or uniform in thickness or may vary in thickness across their surface. Sheets may be a single smooth surface, or they may be meshed or perforated. The micronized form can be resuspended in a solution, such as water or saline solution, prior to implantation or administration to the subject. The resuspended micronized form or powder can be referred to as a slush or slurry.

In embodiments, the graft material including PT can further comprise compositions which provide enhanced mechanical properties, functionality, and/or structure to the graft material. For example, the compositions can provide additional support to the graft material and/or the weakened or damaged tissue, or a scaffold for endogenous cells to populate so to promote healing. As another example, the composition can allow the graft to be more durable than a graft that does not contain the composition and thus prevent graft failure due to mechanical forces. Such compositions can comprise a synthetic mesh, a biological mesh, or a tissue scaffold. In various embodiments, the graft material includes PT, such as PDT, in combination with a synthetic or biological mesh or tissue scaffold. In a further embodiment, the PT may be integrated with the synthetic or biological mesh or tissue scaffold. Integrated may include positioned within, linked, and/or layered or coated with the PT, for example.

Synthetic meshes are man-made compositions formed by the polymerization of a variety of monomers, such as macromolecules comprising polyacrylic acid, polyaspartic acid, polytartaric acid, polyglutamic acid, polyfumaric acid, and so on as well as their salt forms (such as sodium salt and potassium salt). Non-limiting examples of synthetic polymers comprise cyanoacrylate. The synthetic mesh can comprise polyglactin (such as Vicryl mesh), e-PTFE, polypropylene, polyester, polyglycolic, polyester/collagen, polypropylene/PG910, polypropylene/e-PTFE, polypropylene/cellulose, polypropylene/PVDF, polypropylene/sodium hyaluronate, polypropylene/polyglecaprone, polypropylene/titanium, polypropylene/omega 3, BioA, and the like. See, for example, Gillern, Suzanne, and Joshua IS Bleier. "*Parastomal hernia repair and reinforcement: the role of biologic and synthetic materials.*" Clinics in colon and rectal surgery 27.04 (2014): 162-171, which is incorporated by reference herein in its entirety.

Mesh made of synthetic materials can be found in knitted mesh or non-knitted sheet forms. The synthetic materials used can be absorbable, non-absorbable or a combination of absorbable and non-absorbable materials.

Biological mesh are made of non-placental mammalian tissue, such as skin, bladder, or intestine, that has been processed, cross-linked, chemically treated, and/or disinfected to be suitable for use as an implanted device. The biological mesh may or may not be absorbable. The majority of tissue used to produce these mesh implants are from human, pig (porcine) or cow (bovine) source. Biological mesh can comprise biological compositions such as acellular dermal matrix or urinary bladder matrix. See, for example, Gillern, Suzanne, and Joshua I S Bleier. "*Parastomal hernia repair and reinforcement: the role of biologic and synthetic materials.*" Clinics in colon and rectal surgery 27.04 (2014): 162-171, which is incorporated by reference herein in its entirety. For example, the biological mesh can comprise a mesh that was living tissue of human or animal origin, rendered acellular, and comprised of either cross-linked on non-crosslinked proteins. The biological mesh can be partially or completely resorbed.

Biological mesh can also be formed by the polymerization of natural polymers. Natural polymers occur in nature and can be extracted, such as polysaccharides or proteins. Non-limiting examples of polysaccharides comprise chondroitin sulfate, heparin, heparan, alginic acid (alginate), hyaluronic acid, dermatan, dermatan sulfate, pectin, carboxymethyl cellulose, chitosan, melanin (and its derivatives, such as eumelanin, pheomelanin, and neuromelanin), agar, agarose, gellan, gum, and the like as well as their salt forms (such as sodium salt and potassium salt). Non-limiting examples of proteins comprise collagen, alkaline gelatin, acidic gelatin, gene recombination gelatin, and so on.

A tissue scaffold refers to a composition which can act as a structural scaffold, such as a scaffold by which viable cells can readily populate. The term "viable cell" can refer to a cell that is alive and capable of growth, proliferation, migration, and/or differentiation. For example, a tissue scaffold can comprise matrices, such as collagen matrix. The graft material can be mixed with the matrices and the resulting admixture can be applied on top of (overlay) an opening that has been closed with a suture. In some embodiments, cells from the native tissue (e.g., the host subject) can migrate into the tissue scaffold and readily repopulate the graft (and thus promote healing). In embodiments, the graft can be seeded with viable cells so as to repopulate the graft with the viable cells prior to implantation.

In embodiments, the graft material is non-absorbable or substantially non-absorbable, which will remain in the body indefinitely and is considered a permanent implant. It is used to provide permanent reinforcement to the repaired hernia.

In other embodiments, the graft material is absorbable or substantially absorbable, which will degrade over time. It is not intended to provide long-term reinforcement to the repair site. As the material degrades, new tissue growth is intended to provide strength to the repair.

In further embodiments, the graft material can further comprise one or more therapeutics and/or drug agents, such as for the sustained or controlled release of such therapeutics and/or drugs. Such agents can be used to prevent and/or treat progression and/or symptoms of disease (such as those diseases and symptoms described herein), and can also be used to prevent, treat, and or alleviate unwanted side effects of graft implantation. Non-limiting examples of unwanted side effects of implantation or grafting, for example, comprise immune response complications, pain, infection, inflammation, or scarring. Such unwanted side effects can be prevented, treated, or relieved through sustained, controlled, local release of drug and/or therapeutic agents from the polymer or the graft material. For example, the graft materials described herein may include addition of at least one anti-biotic, at least one anti-inflammatory, and/or at least one analgesic and/or anesthetic could prevent infection, reduce local inflammation and decrease pain at the surgical and/or implantation site, thus, for example, providing symptomatic relief.

The graft material, such as PT graft materials, can be mixed, combined, layered, coated, and/or integrated with therapeutic and/or prophylactic agents allowing for sustained release of the therapeutic and or prophylactic agent. Non-limiting examples of such agents comprise antibiotics, pain relievers, anti-inflammatories, or any combination thereof.

"Antibiotic" can refer to an agent that controls the growth of bacteria, fungi, or similar microorganisms, wherein the substance can be a natural substance produced by bacteria or fungi, or a chemically/biochemically synthesized substance (which may be an analog of a natural substance), or a chemically modified form of a natural substance. One of skill will recognize that the scaffold can be coated with a wide variety of antibiotics, such as penicillins, cephalosporins, macrolides, fluoroquinolones, sulfonamides, tetracyclines, aminoglycosides, and the like.

"Pain reliever" can refer to an agent that can provide relief from pain. An analgesic is any member of a group of drugs used to achieve analgesia, i.e., relief from pain. For example, the analgesic can be a pyrazolone derivative, such as (ampyrone, dipyrone, antipyrine, aminopyrine, and propyphenazone), aspirin, paracetamol, a non-steroidal anti-inflammatory (such as Ibuprofen, diclofenac sodium, or naproxen sodium), an opioid (such as codeine phosphate, tramadol hydrochloride, morphine sulphate, oxycodone), or any combination thereof. An anesthetic refers to any member of a group of drugs used to induce anesthesia—in other words, to result in a temporary loss of sensation or awareness of pain. Non-limiting examples of anesthetics comprise benzocaine, chloroprocaine, cocaine, cyclomethycaine, dimethocaine, larocaine, piperocaine, propoxycaine, procaine, novocaine, proparacaine, tetracaine, amethocaine, articaine, bupivacaine, cinchocaine, dibucaine, etidocaine, levobupivacaine, lidocaine, lignocaine, mepivacaine, prilocaine, ropivacaine, trimecaine.

An "anti-inflammatory" refers to a substance that treats or reduces the severity of inflammation and/or swelling. Non-limiting examples of anti-inflammatories comprise steroidal anti-inflammatories (such as corticosteroids) and non-steroidal anti-inflammatories (such as aspirin, celecoxib, diclofenac, diflunisal, ibuprofen, indomethacin, ketoprofen, ketorolac, nabumetone, naproxen, oxaprozin, piroxicam, salsalate, sulindac, tolmetin).

Sustained-release graft materials may have a common goal of improving treatment and/or symptomatic relief over that achieved by their non-controlled counterparts. The use of an optimally designed sustained-release preparation in medical treatment can be characterized by a minimum of drug substance being employed to cure, control, and/or provide relief of the condition in a minimum amount of time. For example, the sustained-release grafts can release an amount of a drug over the course of 1 day, 1 week, 2 weeks, 3 weeks, 4 weeks, 2 months, 3 months, 4 months, 5 months, 6 months, 7 months, 8 months, 9 months, 10 months, 11 months, 12 months, or longer. Advantages of sustained-release formulations include extended activity of the drug, reduced dosage frequency, and increased patient compliance. In addition, sustained-release formulations can be used to affect the time of onset of action or other characteristics, such as blood levels of the drug, and can thus affect the occurrence of side (e.g., adverse) effects.

Most sustained-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released at a rate that will replace the amount of drug being metabolized and excreted from the body. Sustained-release of an active ingredient can be stimulated by various conditions including, but not limited to, pH, temperature, enzymes, water, or other physiological conditions or compounds.

The graft material can comprise growth factors, such as endogenous growth factors, cytokines, chemokines, and protease inhibitors, many of which function to stimulate paracrine responses in fibroblasts, endothelial cells, and stem cells to promote tissue healing and repair. Previous studies have identified over 226 growth factors, cytokines, chemokines, and protease inhibitors, many of which function to stimulate paracrine responses in fibroblasts, endothelial cells, and stem cells to promote tissue healing and repair. In addition, these bioactive factors, including epidermal growth factor (EGF), fibroblast growth factor-4 (FGF-4), and TGF-$\beta$1 are known to promote proliferation, migration, and secretion of paracrine factors by fibroblasts, endothelial cells, and a variety of adult stem cells, including bone marrow-derived mesenchymal stem cells, adipose-derived stem cells and hematopoietic stem cells. In a mouse subcutaneous implant model, increased hematopoietic stem cell recruitment and enhanced angiogenesis was demonstrated in response to dHACM implants. These studies demonstrate that dHACM contains active growth factors and other biomolecules that retain the ability to direct or supplement biological activity, for example, by regulating endogenous cells in a wound environment. Non-limiting examples of such growth factors such as EGF, FGF-4, and TGF-$\beta$1.

As introduced above, aspects of the present disclosure are directed towards methods of implanting a graft material in a subject to promote fascial healing; prevent and/or reduce hernia occurrence, development, and/or hernia recurrence; and/or prevent the failure of hernia repair or retard development of a failed hernia repair. Such aspects may be particularly applicable to subjects who are suffering from a hernia and subjects who are at risk of developing a hernia.

The term "subject" or "patient" can refer to any organism to which aspects of the present disclosure can be administered, e.g., for experimental, diagnostic, prophylactic, and/or therapeutic purposes. Typical subjects to which compounds of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. The term "living subject" refers to a subject noted above or another organism that is alive. The term "living subject" refers to the entire subject or organism and not just a part excised (e.g., a liver or other organ) from the living subject.

Subjects at risk of developing a hernia refers to a subject who has a significantly greater risk of developing a hernia than the average risk of an age-, and sex-matched individual from the general population. See, for example, Ahn, Byung-Kwon. "*Risk Factors for Incisional Hernia and Parastomal Hernia after Colorectal Surgery.*" Journal of the Korean Society of Coloproctology 28.6 (2012): 280, which is incorporated by reference herein in its entirety.

For example, subjects at risk of developing a hernia may comprise those who are obese, afflicted with an infection (such as a surgical site infection, intra-abdominal infection, deep tissue infection, or superficial abdominal infection), underwent a bowel resection, underwent colon surgery, are being administered corticosteroids, smokes, has chronic obstructive pulmonary disease, malnutrition, diabetes, immunosuppression, anemia, hypoproteinemia, male gender, old age, increased abdominal pressure (such as coughing, vomiting, distention, and ascites), or any combination. For example, subjects at risk of developing a hernia include those who are undergoing surgical incision of the abdominal wall, subject who are both with a congenital hernia, and/or subject who participate in activities that predisposes them to hernias, such as sports hernias or excessive coughing.

In the case or incisional hernias, methods described herein can be performed during the procedure which requires the incision. In the case of a procedure requiring incision in an abdominal wall, methods described herein can be performed after the incision is made. The methods can be performed before the incision is closed or after the incision is closed.

Implanting the graft material may align the material with an opening in the abdominal wall. This may be particularly suitable when the graft material is provided as a sheet or sheet-like composition. For example, the graft material may be generally placed or arranged in a position so to generally mirror the opening, such as the surgical incision. Thus, the graft material can promote healing of the surgical incision, such as healing of the abdominal fascial edges.

In one embodiment, implanting the graft material may not necessarily include the graft material actively affixed to the tissue to promote healing, but instead the graft material may be placed as an overlay or underlay in contact with or in close proximity to the opening. For example, the graft material can be implanted over or ventral to an abdominal wall opening, and thus promote healing of the opening. In other embodiments, the graft material can be implanted superficial to an abdominal wall opening, and thus promote healing of the opening. In a particular embodiment, graft material including PT, such as dHACM or other PDT, is placed directly on top of (overlay) an abdominal fascia incision that has been closed with suture, and the dHACM or other PDT is not secured. The subcutaneous fat and skin are then closed over the graft material.

In an alternative embodiment, the graft material or portion thereof can be anchored to the opening, such as an opening in the abdominal wall. The graft material can be anchored to the tissue opening by fasteners known to the skilled artisan, such as by pressure, an adhesive (such as fibrin glue), a clip, a tack, a suture, a staple, or a screw. For example, the graft material is implanted under, deep to, or dorsal to the abdominal wall opening, such as by sutures.

In embodiments, the opening, such as the abdominal wall opening, can be substantially or completely closed prior to implanting of the graft material. In a particular embodiment, dHACM or other PDT is secured with sutures, staples, screws, or other securement devices under (underlay or sublay) an abdominal fascia incision that has been closed with suture. The subcutaneous fat and skin are then closed over the incision.

Surgical mesh, such as a synthetic mesh or biological mesh, is a currently available tool in hernia repair; however, are fraught with postoperative complications. Common complications include infection, pain, adhesions, seroma mesh extrusion and hernia recurrence. Reducing the complications of mesh implantation is of utmost importance given that hernias occur in hundreds of thousands of patients per year in the United States. Thus, in an embodiment, the opening is closed with a surgical mesh, and the graft material is placed or affixed over the surgical mesh or affixed to the undersurface ("underlay") of the surgical mesh to promote healing of the tissue and reduce unwanted side effects. In a particular embodiment, a hernia defect is closed with synthetic mesh, and dHACM or other PDT (either as intact sheets, micronized form, or powder form, or a combination thereof) is placed on top of areas where the mesh interfaces with the fascia, or under areas where the mesh interfaces with the fascia, or under areas where the mesh interfaces with the abdominal cavity and its contents (e.g. large/small intestine/other intraabdominal organs such as liver, stomach, spleen). The dHACM or other PDT may or may not be secured with sutures, staples, screws, or other securement devices. The subcutaneous fat and skin are then closed over the dHACM or other PDT and mesh.

In another embodiment, the opening, such as the abdominal wall opening, can be substantially or completely closed after implanting the graft material. For example, the graft material can be placed or affixed under the opening, and then the opening can be substantially or completely closed, thereby allowing the graft material to promote healing of the tissue.

The breakdown of a hernia repair is called recurrent hernia. The bulge returns at or near the site of the prior hernia. Recurrent hernias greatly increase the complexity of subsequent repair. If left untreated, severe complications can result such as the intestines being trapped known as an incarcerated hernia, digestive obstruction, or a loss of blood supply to the intestines known as a strangulated hernia. Thus, aspects of the present disclosure are directed towards a method of preventing hernia recurrence.

As described herein, graft material comprising PT may be utilized to significantly reduce incisional hernia rates. For example, testing embodiments in 10 human subjects who were at high risk for developing hernias following celiotomies and stoma surgeries, the PT completely prevented the development of all hernias (0% hernia formation) (see Example 10 below).

Examples are provided herein to facilitate a more complete understanding of the present disclosure. The examples illustrate experimental validation and exemplary modes of making and practicing the present disclosure. However, the scope of the present disclosure is not limited to specific embodiments disclosed in these Examples, which are for purposes of illustration only, since alternative methods can be utilized to obtain similar results.

EXAMPLES

Example 1: PT Sheets

Graft material comprising one or more PT sheets may be used in the below applications. The PT may include processed or unprocessed amnion, chorion, umbilical cord vein, Wharton's jelly, or combinations thereof such as dHACM, cryopreserved umbilical cord and amniotic membrane or membrane matrix, processed and/or unprocessed amniotic membrane and/or chorionic membrane, processed and/or unprocessed umbilical cord, processed and/or unprocessed umbilical cord and processed and/or unprocessed amniotic membrane and/or chorionic membrane, etc. The one or more PT sheets may or may not be secured with sutures, staples, screws, or other securement device. The subcutaneous fat and skin may then be closed over the PT graft material. In some embodiments, the PT graft material comprises dHACM or any other PDT disclosed herein.

In one application, the PT graft material may be placed directly on top of (overlay) an abdominal fascia incision that has been closed with suture.

In another application, the PT graft material is secured with sutures, staples, screws, or other securement devices under (underlay or sublay) an abdominal fascia incision that has been closed with suture.

In another application, the PT graft material may be placed directly on top of (overlay) an abdominal fascia defect that has not been completely closed with any surgical devices. Such defects include abdominal wall openings for stomas, ostomies, surgical drains, feeding tubes, etc.

In another application, the PT graft material may be placed directly on top of (overlay) a hernia defect that has been or that has not been completely closed by any surgical devices.

In another application, the PT graft material may be secured with sutures, stables, screws, or other securement devices under (underlay or sublay) a hernia defect that is then closed.

Example 2: Micronized or Powdered PT

Graft material comprising micronized or powdered PT. The PT may include processed or unprocessed amnion, chorion, umbilical cord vein, Wharton's jelly, or combinations thereof such as dHACM, cryopreserved umbilical cord and amniotic membrane or membrane matrix, processed and/or unprocessed amniotic membrane and/or chorionic membrane, processed and/or unprocessed umbilical cord, processed and/or unprocessed umbilical cord and processed and/or unprocessed amniotic membrane and/or chorionic membrane, etc. The PT graft material is spread or scattered over an abdominal fascia incision that has been closed with suture. The subcutaneous fat and skin are then closed over the PT graft material. In one example, the PT graft material includes micronized or powdered dHACM or any other PDT, such as those described herein.

Example 3: Solubilized or Dissolved PT

Graft material comprising solubilized or dissolved PT may be used in the below applications. The PT may include processed or unprocessed amnion, chorion, umbilical cord vein, Wharton's jelly, or combinations thereof such as dHACM, cryopreserved umbilical cord and amniotic membrane or membrane matrix, processed and/or unprocessed amniotic membrane and/or chorionic membrane, processed and/or unprocessed umbilical cord, processed and/or unprocessed umbilical cord and processed and/or unprocessed amniotic membrane and/or chorionic membrane, etc. In one example, the PT includes solubilized/dissolved dHACM or any other PDT, such as those described herein.

In one application, PT graft material is injected within about 4 cm, for example, of an abdominal fascia incision that has been closed with suture. The subcutaneous fat and skin may then be closed over the incision.

In another application, solubilized/dissolved PT is mixed with a collagen matrix. The resulting admixture may be applied on top of (overlay) an abdominal fascia incision that has been closed with suture. The subcutaneous fat and skin may then be closed over the mixture.

Example 4: PT Synthetic Mesh

Graft material comprising PT in the form of one or more intact sheets, micronized form, powder form, or combination thereof, may be used in conjunction with synthetic mesh in the below applications. The PT may include processed or unprocessed amnion, chorion, umbilical cord vein, Wharton's jelly, or combinations thereof such as dHACM, cryopreserved umbilical cord and amniotic membrane or membrane matrix, processed and/or unprocessed amniotic membrane and/or chorionic membrane, processed and/or unprocessed umbilical cord, processed and/or unprocessed umbilical cord and processed and/or unprocessed amniotic membrane and/or chorionic membrane, etc. In one example, the PT may include dHACM or any other PDT, such as those described herein. In application, a hernia defect is closed with synthetic mesh and the PT graft material is placed on top of areas where the mesh interfaces with fascia.

In another application, a hernia defect is closed with synthetic mesh and the PT graft material is placed under areas where the mesh interfaces with the fascia.

In another application, a hernia defect is closed with suture and reinforced with synthetic mesh (onlay or overlay). The PT graft material is placed on top of areas where the mesh interfaces with the fascia incision line.

In another application, the PT graft material and synthetic mesh may be employed as described in any of the above applications to prevent or reduce occurrence of a hernia or development of a hernia rather than to repair or treat a hernia defect. For example, a patient who does not have a hernia may present a gunshot wound to the abdomen. A laparotomy may be performed, wherein the patient is determined to be high risk for hernia formation due to emergency, obesity, blood loss, etc. and the PT graft material and synthetic mesh are used concomitantly to prevent hernia formation. In one example, the patient is determined to be at high risk of developing a hernia.

In the above applications, the PT graft material may or may not be secured with sutures, staples, screws, or other securement device. The subcutaneous fat and skin are then closed over the PT graft material.

Example 5: PT Biological Mesh

Graft material comprising PT may be utilized in conjunction with a biological mesh. The PT may comprise one or more intact sheets, micronized form, powder form, or combination thereof. The PT may include processed or unprocessed amnion, chorion, umbilical cord vein, Wharton's jelly, or combinations thereof such as dHACM, cryopreserved umbilical cord and amniotic membrane or membrane matrix, processed and/or unprocessed amniotic membrane and/or chorionic membrane, processed and/or unprocessed umbilical cord, processed and/or unprocessed umbilical cord and processed and/or unprocessed amniotic membrane and/or chorionic membrane, etc. In one example, the PT may also comprise dHACM or any other PDT, such as those described herein.

In one application, a hernia defect is closed with biological mesh. The PT graft material may be placed on top of areas where the mesh interfaces with the fascia. The PT graft material may or may not be secured with sutures, staples, screws, or other securement device. The subcutaneous fat and skin are then closed over the PT graft material.

In another application, a hernia defect is closed with biological mesh. The PT graft material is placed under areas where the mesh interfaces with the fascia. The PT graft material may or may not be secured with sutures, staples, screws, or other securement devices.

In another application, a hernia defect is closed with suture and reinforced with biological mesh (onlay or overlay). The PT graft material is placed on top of areas where the mesh interfaces with the fascia incision line. The PT graft material may or may not be secured with sutures, staples, screws, or other securement device. The subcutaneous fat and skin are then closed over the PT graft material.

In another application, the PT graft material and biological mesh may be employed as described in any of the above applications to prevent or reduce occurrence of a hernia or development of a hernia rather than to repair or treat a hernia defect. For example, a patient who does not have a hernia may present a gunshot wound to the abdomen. A laparotomy may be performed, wherein the patient is determined to be risk for hernia formation due to emergency, obesity, blood loss, etc. and the PT graft material and biological mesh are used concomitantly to prevent hernia formation. In one example, the patient is determined to be at high risk of developing a hernia.

Example 6: Combination PT Interventions

The methodologies described above in Examples 1-5 and elsewhere herein are not exclusive as the various methodologies may be used in combination. For example, dissolved/solubilized PT may be injected at or proximate to an incision and micronized and/or powdered PT may be spread or scattered over an incision, such as an abdominal fascia incision, synthetic mesh, or biological mesh. The methodologies described herein may be applied prophylactically or with respect to hernia repair. For example, the PT graft material may be utilized prophylactically to prevent or limit occurrence of a hernia or development of a hernia that subsequently occurs. The PT graft material may also be utilized in original or recurrent hernia repair to prevent or limit reoccurrence of a hernia or development of a recurrent hernia.

Example 7

Employing a double-blind, prospective randomized control trial (RCT) a validated, acute IH model was used to study the ability of PT graft material including dHACM to prophylatically prevent or reduce occurrence and/or development of IH. The model is associated with approximately a 83% hernia rate.

Methods: For the study 400 gram, 20-week-old male Sprague-Dawley rats were randomized to 1 of 4 treatment groups (N=10 per group):
1) micronized injectable dHACM (dHACM injection),
2) saline injection
3) dHACM sheets (dHACM sheet overlay) (Amniofix®, Mimedx Group, Inc, Marietta, GA)
4) control (no treatment).

Each rat received a 5 cm midline laparotomy incision, an example incision is provided in FIG. 1, followed by closure. Incisions and closures were performed by a surgeon blinded to group assignment. The incisions were closed with interrupted 5-0 plaingut sutures×3. A separate surgeon administered the intervention.

A primary endpoint used was IH formation measured on post-operative day (POD) 28 by surgeons blinded to group assignment. IH size was also used as a primary endpoint. Secondary endpoints included: fascia tensile strength, collagen I/IIII ration, serum inflammatory markers, and tissue inflammatory marker expression.

Figure 2:
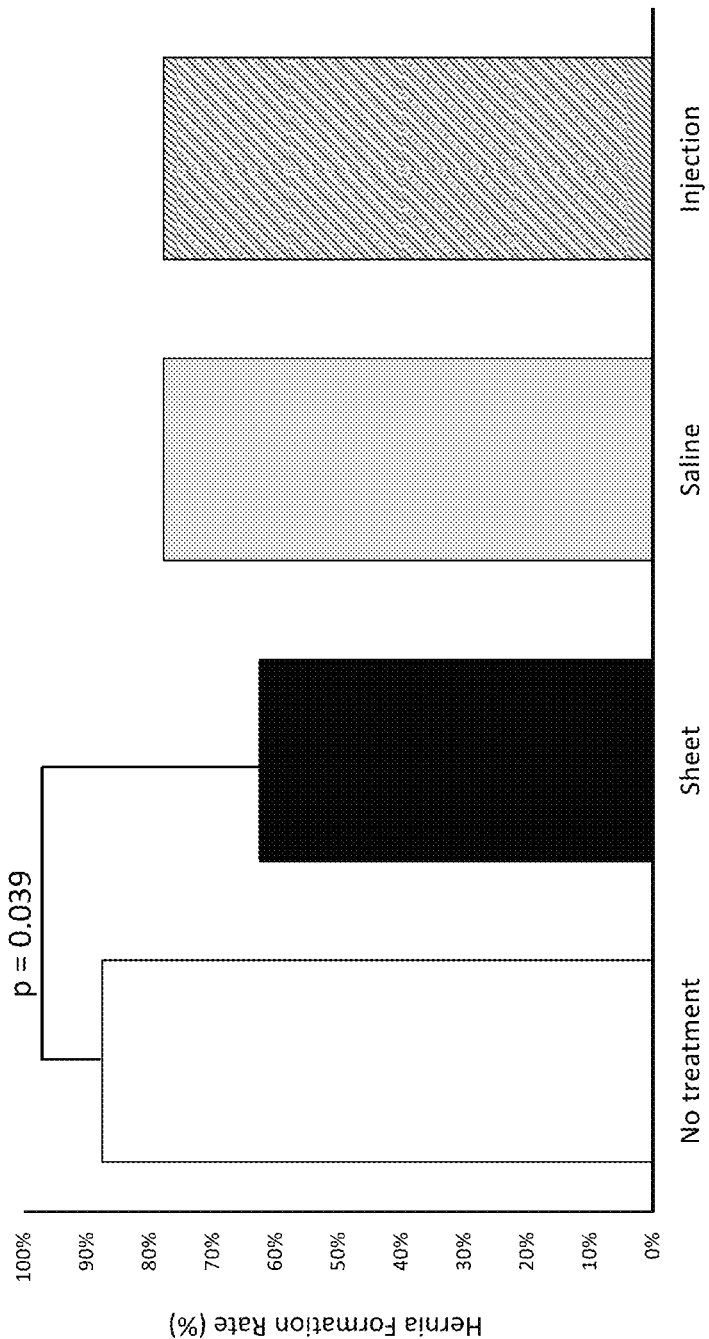
FIG. 2 shows dHACM sheets significantly reduce incisional hernia formation.
Figure 3:
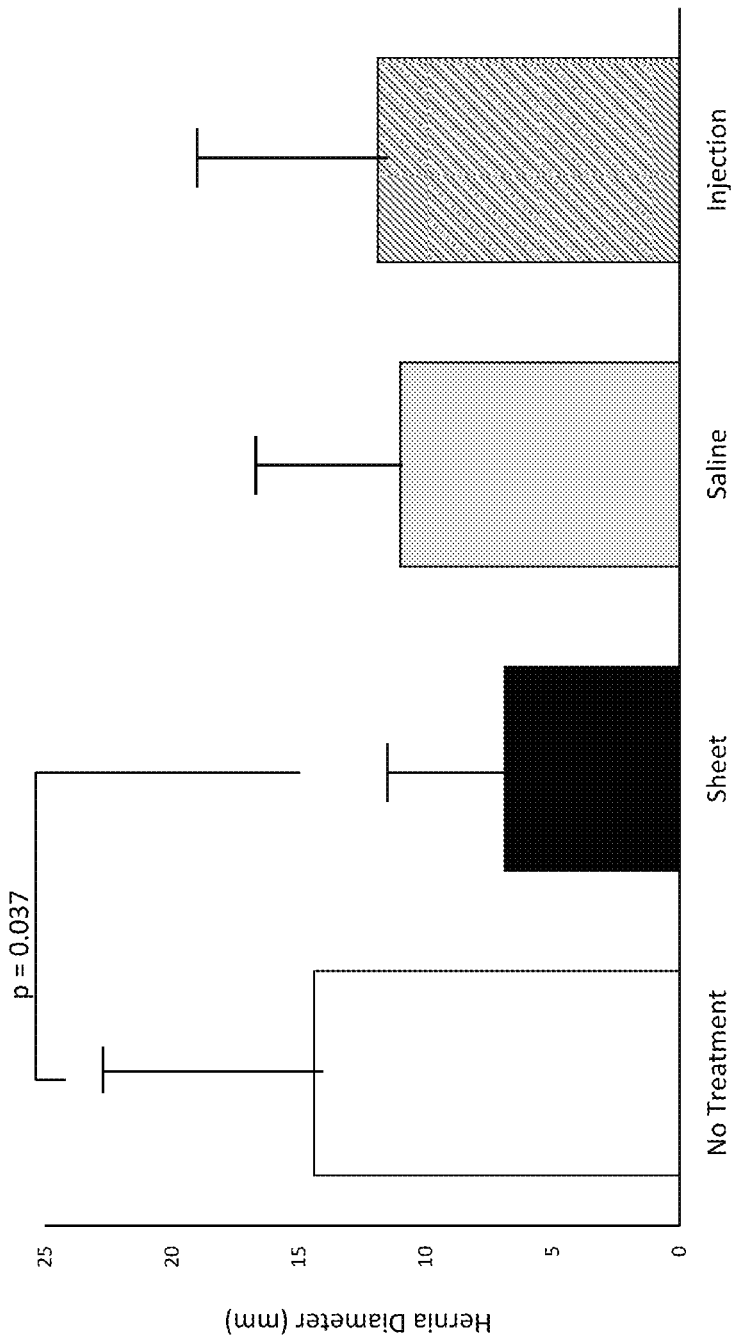
FIG. 3 shows dHACM sheets significantly reduce hernia diameter.

Results: Overall, 26 of 34 rats (76.4%) developed IH. Referring to FIG. 2, only dHACM sheets significantly reduced IH formation (62.5% vs. 87.5% control; p=0.04). Referring to FIG. 3, dHACM sheets decreased IH size/diameter (6.9 mm vs. 14.4 mm control; p=0.04).

Secondary endpoints showed no statistically significant difference between groups. However, tensile strength trended stronger in the sheet group (1.02 N/mm2 vs. 0.89 N/mm2 control; p=0.33). Serum CRP & IL-6 levels also trended higher with sheets, but tissue IL-6 trended lower with sheets.

These studies indicate that PT graft material prophylactically prevent development or reduce the occurrence of IH formation and size as dHACM sheets significantly reduce hernia rates and hernias that do form are smaller than those occurring without PT intervention treatment.

Example 8

A double-blind, prospective randomized controlled trial (RCT) of PT to prevent acute IH in a previously validated rat model was performed. The PT graft material used for the trial was dHACM. dHACM is available in two forms: implantable sheet and micronized injectable. Thus, the groups of intervention and matching controls were (A) No Treatment vs. Sheet, and (B) Saline vs. Injection.

Methods: All procedures were performed in accordance with and approved by the Institutional Animal Care and Use Committee and the Institutional Review Board. The rat IH model used in our study has been previously validated as a model of acute IH. (Franz M G. Kuhn M A, Nguyen K, et al. "*Transforming growth factor beta 2 lowers the incidence of incisional hernias.*" J Surg Res. 2001; 97:109-116; Korenkov, M. et al. "*Local administration of TGF-β1 to reinforce the anterior abdominal wall in a rat model of incisional hernia.*" Hernia. 2005; 9:252-258; Islam K N, Bae J W, Gao E, et al. "*Regulation of nuclear factor κB (NF-κB) in the nucleus of cardiomyocytes by G protein-coupled receptor kinase 5 (GRK5).*" J Biol Chem. 2013; 288(50):35683-9)

Forty 16-week-old male Sprague-Dawley rats (Charles River) weighing 400 g were acclimated to laboratory conditions for 2 weeks. Rat chow and water were provided ad libitum. Each animal was randomized (Research Randomizer Version 4.0) to 1 of 4 surgical treatments (N=10 per treatment): 1) Sheet: 5 cm×1 cm dHACM sheets overlaid on the celiotomy incision, 2) No Treatment, 3) Injection: 10 mg micronized dHACM dissolved in 1 mL sterile saline and injected along the fascial incision prior to incision, or 4) Saline: 1 mL sterile saline injected along the fascial incision prior to incision.

A double-blind design was used. The surgeon performing the celiotomy and fascial repair was unaware of the assigned treatment. The intervention was administered by a second surgeon. Evaluation of hernia formation and other experimental endpoints were performed by individuals unaware of treatment.

Anesthesia was induced and maintained with isoflurane via nose cone. The abdomen was prepped by removing fur with electric clippers and disinfected with 2% chlorhexidine gluconate in 70% isopropyl alcohol (Chloraprep). All surgical procedures were performed using aseptic technique. A 6 cm paramedian incision was made 2 cm lateral to the midline. A skin flap was raised via dissection of the avascular prefascial plane, exposing the linea alba. A 5 cm celiotomy incision was then made, taking care not to injure underlying structures. An intraperitoneal dose of Buprenex SR at 1 mg/kg was given for analgesia. The fascia was then closed using three interrupted 5-0 plain gut sutures placed at equal intervals across the celiotomy incision.

A second surgeon then performed the treatment as detailed above. The skin incision was closed using 3-0 nylon running locking sutures to minimize the risk of evisceration. The animals were recovered from anesthesia in fresh clean cages and were not returned to the animal housing unit until ambulation was observed. Post-operatively, prophylactic sulfamethoxazole/trimethoprim at 160 mg/36 mg was given orally for 7 days. Animals were monitored by both study staff and veterinary staff daily during the first post-operative week and bi-weekly during post-operative weeks 2-4 for the development of discomfort, illness, and incisional complications such as evisceration or IH.

Figure 11:
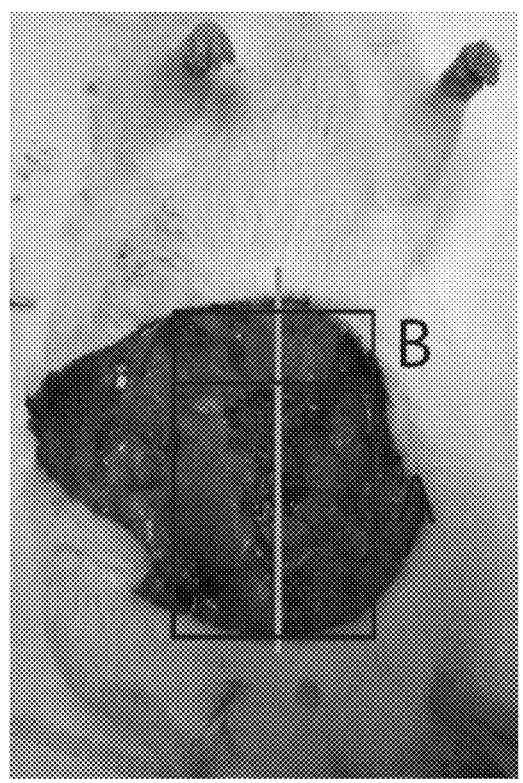
FIG. 11 shows a diagram of abdominal wall specimen apportionment at 28 days after celiotomy. Green line demonstrates the midline. A hernia is visible in this version. Segment A is 4 cm in length, was immediately stored at −80° C. and eventually sent for tensiometry. Segment B was further divided in half; 0.5 cm of length was immediately stored at −80° C. and ultimately used for qRT-PCR and Western blotting. Another 0.5 cm of length was immediately placed in 10% formalin for histology.

On post-operative day (POD) 28, the surviving rats were euthanized via carbon dioxide. The ventral abdominal wall was excised, and peritoneal and subcutaneous surfaces of the fascia were inspected for IH formation. Hernia formation was defined as a 2 mm minimum opening in the fascia. The fascia was then divided into a 4 cm-wide strip for tensile strength testing, and two 0.5 cm-wide strips for molecular and histological analyses (FIG. 11). The 4 cm strip and one 0.5 cm strip were immediately stored in −80° C. until tensiometric testing and molecular analyses, respectively.

The remaining 0.5 cm strip was fixed in 10% formalin for histological analysis. Sample preparation, data collection, and analysis were performed by study staff unaware of treatment.

Tensiometric testing was performed. Specimens were defrosted in normal saline until they reached room temperature (23° C.). Segments of abdominal wall including celiotomy scar and any hernias were clamped in pneumatic versa grips with serrated faces (Instron, Canton, MA) 15 mm apart (7.5 mm from each side of the linea alba). One of the grips was attached to the load cell of a materials testing system (8841 Dynamite, Instron). Tensile loading was orthogonal to the direction of the celiotomy scar. Samples were loaded to 1 N of in situ pretension along the sagittal axis for 60 seconds. Samples were then preconditioned with 10 cycles of 6% vertical strain applied at 0.5 mm/sec by displacement control. Following preconditioning, a 1 N preload was applied again for 60 seconds and then samples were loaded to failure at 10 mm/sec in a single cycle under displacement control. Load displacement data was recorded at 10 Hz. Samples were moistened with normal saline at regular intervals over the testing process. Tension loading was digitally recorded with a high-definition digital camera (Alpha 6500, Sony). Tissue failure was defined as visible rupture of the midline scar and was correlated with the maximal recorded tension. Tensile strength per sample was normalized to the cross-sectional area of the sample.

Real-time quantitative polymerase chain reaction (RT-qPCR), peri-celiotomy scar tissue was analyzed to determine expression levels of inflammatory markers IL-6, metalloproteinases (MMP) 1 and 13. RNA was prepared from rat peri-celiotomy scar tissue via Trizol RNA isolation.

Sample concentration and purity were assessed using NanoDrop (Thermo Fisher). All RT-qPCR was performed on an iCycler (Bio-Rad) using a QuantiTect SYBR Green RT-PCR Kit (QIAGEN). RNA was diluted for a final input of 10 ng per reaction. Samples were spiked with 10 nM fluorescein (Sigma), and reactions were performed with primer sequences: IL-6 (forward 5'-ACTTCACAAGTCG-GAGGCTT-3' (SEQ ID NO 1); reverse 5'-AGTGCAT-CATCGCTGTTCAT-3' (SEQ ID NO 2)), MMP 1 (forward 5'-GGAACAGATACGAAGAGGAAACA-3' (SEQ ID NO 3); reverse 5'-TGTTTCCTCTTCGTATCTGTTCC-3' (SEQ ID NO 4)) and MMP 13 (forward 5'-TCTGCACCCTCAGCAGGTTG-3' (SEQ ID NO 5); reverse 5'-CAACCTGCTGAGGGTGCAGA-3' (SEQ ID NO 6)); β-actin (forward 5'-AGCCATGTACGTAGCCAT-3' (SEQ ID NO 7); reverse 5'-CTCTCAGCTGTGGTGGT-GAA-3' (SEQ ID NO 8)). $2^{\Delta\Delta}$ cycle threshold (Ct) was used for analysis.

On POD 2 and 5, 200-300 μL plasma was collected from each rat via tail or saphenous vein phlebotomy. Collection was performed under anesthesia to reduce the risk of inducing acute IH, skin incision dehiscence, and evisceration. Plasma levels of inflammatory markers C-reactive protein (CRP) and interleukin-6 (IL-6) were quantified using ELISA (CRP: MyBiosource, catalogue number MBS2508830; IL-6: MyBiosource, catalogue number MBS 355410).

Semi-quantitative analysis of peri-celiotomy scar tissue levels of collagen I and III levels were determined by Western blots. Collagen was extracted from 0.5×0.5 cm region of scar tissue. Minced tissue was stirred in a buffer containing 150 mM NaCl, 50 mM Tris-HCl, pH 7.5, 1% SDS, 1% nonidet p40, and sodium deoxycholate for 2 hours on ice and centrifuged for 10 minutes. Supernatant containing collagen was analyzed by immunoblotting using antibodies specific to collagen I, collagen III (Abcam), and GAPDH (Santa Cruz Biotechnology). GAPDH was used as loading control. The image of the protein band was visualized and scanned by an infrared imaging system (Odyssey). Image J (image processing software developed at the NIH) was used for the quantification of the scanned image.

Categorical variables were analyzed for statistical significance (p<0.05) using chi-square testing (SPSS). Continuous variables were analyzed for statistical significance (p<0.05) using independent t-tests (SPSS).

Results: Overall, 34 of 40 (85%) rats survived until POD 28 (the experimental endpoint). The cause of death in all 6 cases was evisceration within the first 5 POD. Mortality numbers did not significantly differ between treatments; Group A: 2 animals each in Sheet and No Treatment, and Group B: 1 animal each in Injection and Saline.

Figure 5:
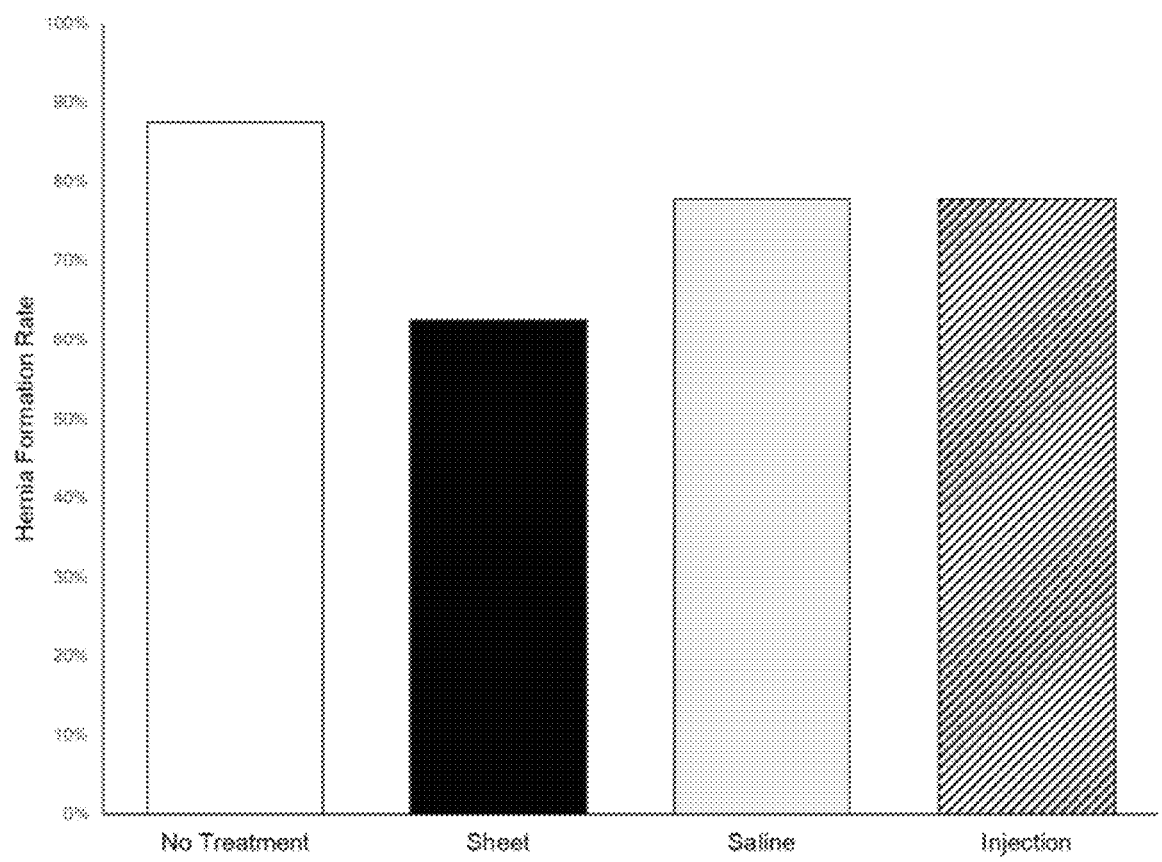
FIG. 5 shows dHACM sheets significantly reduced IH formation. In Group A (No Treatment vs. Sheet), dHACM sheets significantly reduced the IH rate from 87.5% to 62.5% (RR=0.71, p=0.039, $\chi 2$ (2, N=17)). In Group B (Saline vs. Injection) the IH rate was identical between control vs. treatment (77.8%).

With respect to primary endpoints: hernia formation and size, overall, 79.4% (27 of 34) of rats developed IH (FIG. 5). In Group A, the Sheet intervention significantly reduced the IH rate to 62.5% vs. 87.5% in the No Treatment control (RR=0.71, p=0.039). In Group B, Injection and Saline yielded identical IH rates (77.8% for both). In Group A, the average hernia diameter was significantly reduced in Sheet (6.9 mm+/−6.01 mm) vs. No Treatment controls (14.4 mm+/−8.3 mm; p=0.037, FIG. 6). In Group B, average hernia diameter did not significantly differ between Injection (11.67 mm+/−8.78 mm) and Saline (10.22 mm+/−6.67 mm).

Figure 7:
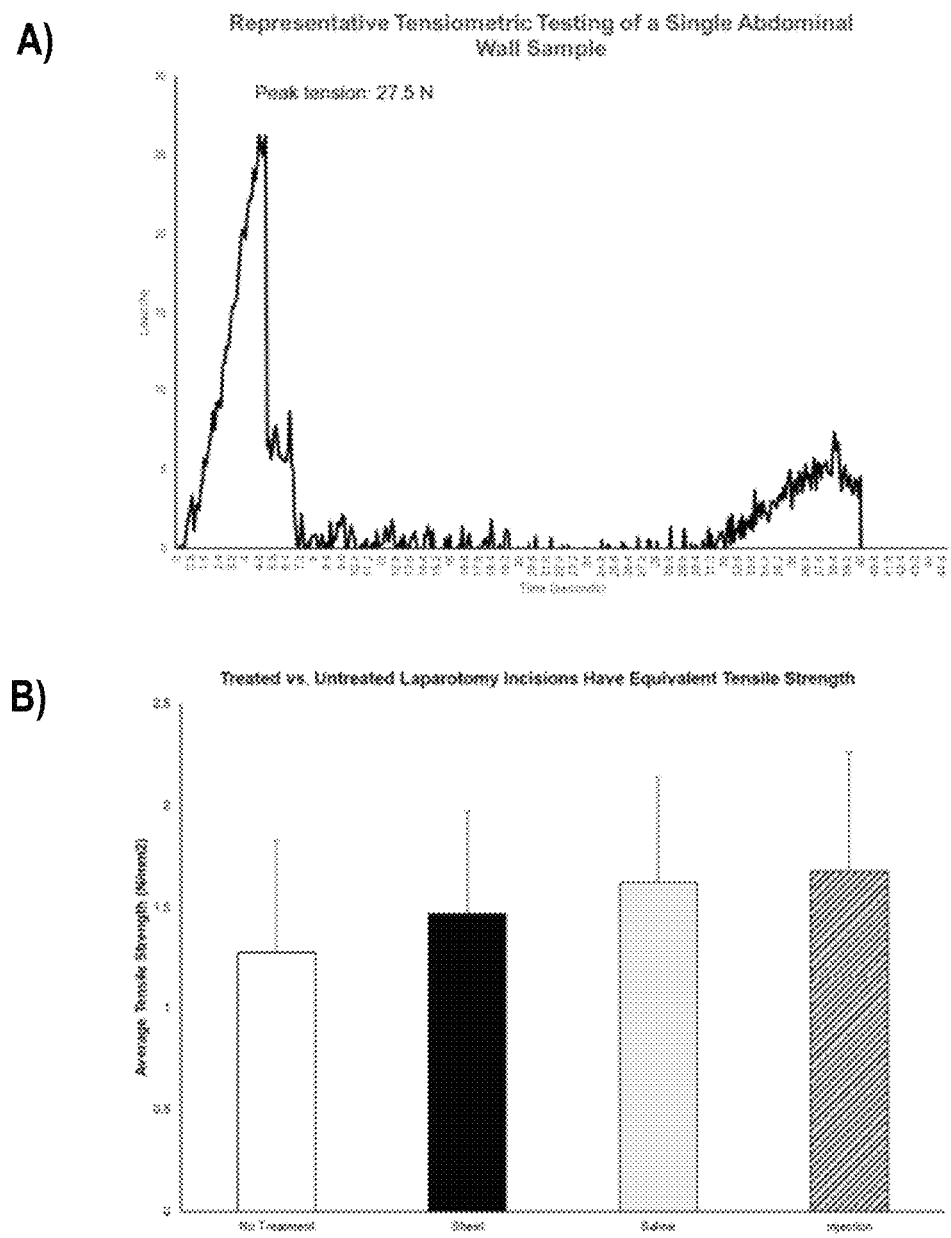
FIG. 7 shows dHACM treated fascia was not weaker than untreated fascia. A) Representative tensiometric testing of a single abdominal wall sample. Testing was performed using an automated system (8841 Dynamite, Instron) loading the system 10 mm/sec orthogonal to the linea alba in a single cycle under displacement control. Load displacement data was recorded at 10 Hz. The peak tension that each sample could sustain was recorded. B) Peak tension was normalized to sample cross-sectional area. In Group A (No Treatment vs. Sheet), mean tensile strengths were No Treatment 0.89 N/mm2 vs. Sheet 1.02 N/mm2. In Group B (Saline vs. Injection) mean tensile strengths were Injection 1.15 N/mm2 vs. Saline 1.55 N/mm2.

Tensile strength of the fascial scar was defined as the load per mm$^2$ at which the fascia began to rupture (FIG. 7, panel A). No significant statistical differences in tensile strength between treatments in either Group A or Group B were identified (FIG. 7, panel B).

Figure 8:
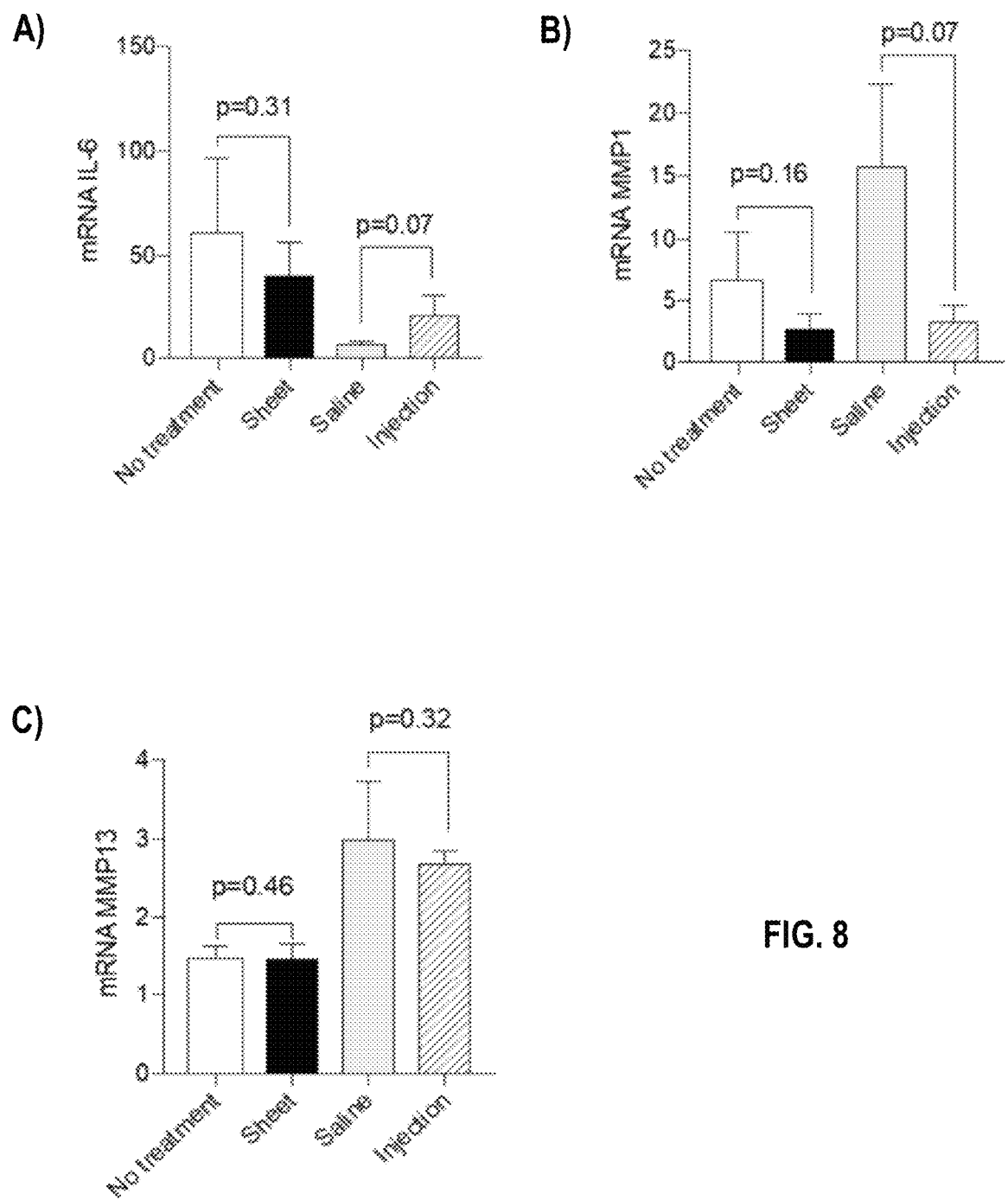
FIG. 8 shows dHACM treatments did not significantly change fascial scar expression of inflammatory markers at 28 days after celiotomy. Expression levels were normalized to the housekeeping gene β-actin. A) In Group A (No Treatment vs. Sheet), mean fascial scar expression levels of IL-6 were: No treatment 61.22+/−35.76 vs. Sheet 40.81+/−15.57 (p=0.31). In Group B (Saline vs. Injection) the expression levels were Saline 7.35+/−1.70 vs. Injection 21.58+/−9.01 (p=0.07). B) In Group A (No Treatment vs. Sheet), mean fascial scar expression levels of MMP-1 were: No treatment 6.80+/−3.76 vs. Sheet 2.77+/−1.17 (p=0.16). In Group B (Saline vs. Injection) the expression levels were Saline 15.37+/−7.80 vs. Injection 3.36+/−1.26 (p=0.07). C) In Group A (No Treatment vs. Sheet), mean fascial scar expression levels of MMP-13 were: No treatment 1.49+/−0.15 vs. Sheet 1.47+/−0.19 (p=0.16). In Group B (Saline vs. Injection) the expression levels were Saline 2.99+/−0.74 vs. Injection 2.69+/−0.15 (p=0.07).

Expression levels of inflammatory markers IL-6, MMP 1, MMP 13 in the fascial scar on POD 28 were measured by RT-qPCR. No statistically significant differences were identified between treatments in either Group A or Group B (FIG. 8).

Plasma levels of the inflammatory markers IL-6 and CRP were measured on POD 2 and 5. No significant statistical differences were identified between treatments in either Group A or Group B at either time point (FIG. 9).

Western blots of collagen I and III levels in the celiotomy scar revealed that there were no significant differences between treatments in either Group A or Group B (FIG. 10). Mean collagen I/III ratios±SD were: No Treatment 1.02±0.51 vs Sheet 1.67±2.16 (Group A) and Saline 1.18±0.51 vs. Injection 1.45±1.36 (Group B).

Figure 6:
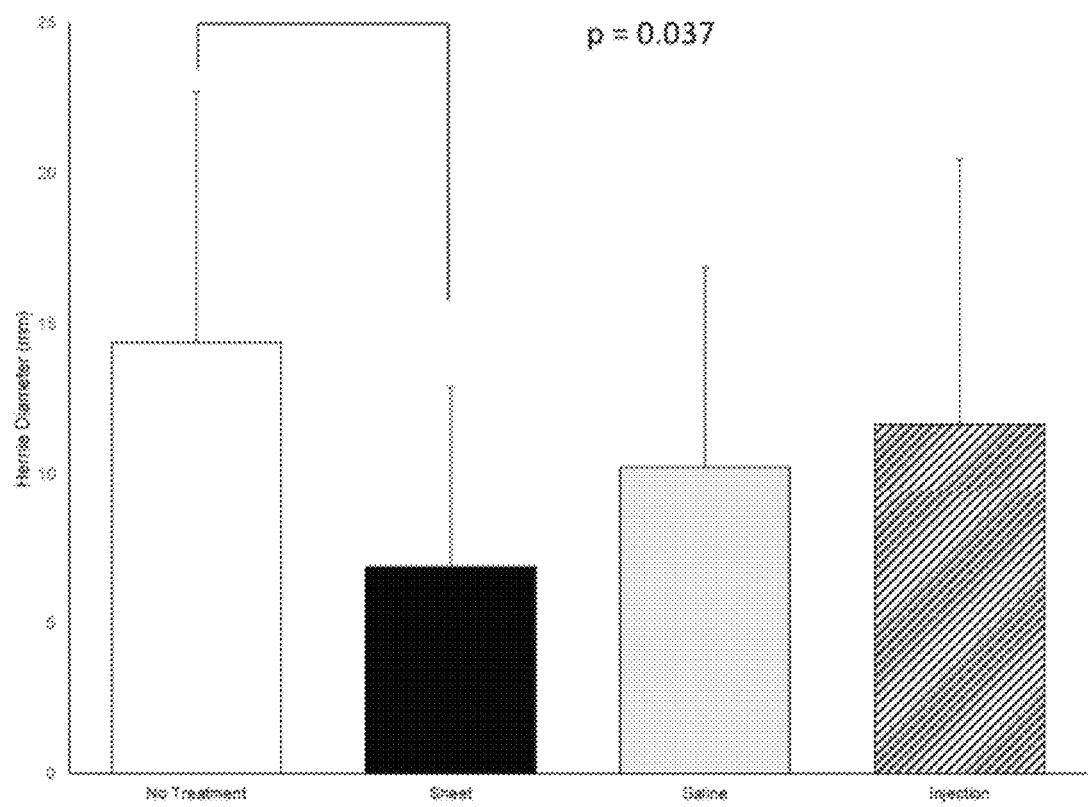
FIG. 6 shows dHACM sheets significantly reduced IH diameter. Overall, 79.4% (27 of 34) of rats developed IH. In Group A (No Treatment vs. Sheet) dHACM sheets significantly reduced the mean IH diameter to 6.9+/−6.0 mm compared to No Treatment 14.4+/−8.3 mm (p=0.039). In Group B (Saline vs. Injection) the IH diameter did not significantly differ between Saline 10.2+/−6.7 mm vs. Injection 11.7+/−8.8 mm (p=0.37).

Consistent with previous studies using this model, 87.5% of the untreated animals in this study developed IH. In this study, animals treated with PT sheets comprising (dHACM) gained a 28.5% relative risk reduction. Moreover, when IH did form, the development was limited wherein the IH were 77.0% smaller in PT-treated animals (FIG. 6). This is noteworthy because larger IH are more difficult to repair and more likely to recur. Molecular characterization of the celiotomy scars shows that the PT-treated scars tended towards greater tensile strength, lower inflammatory markers, and improved collagen I/III ratios (FIGS. 7, 8, 10). Together, these gross and molecular data indicate that PT graft material including dHACM sheets reduce occurrence and development of incisional hernia formation and support use of PDT sheets for use as a novel, safe, and effective prophylactic intervention for IH.

Our molecular characterization of dHACM-treated fascial scar demonstrated trends towards increased greater tensile strength, lower inflammatory markers, and improved collagen I/III ratios (FIGS. 7, 8, 10). The molecular basis for fascial weakness has previously been characterized as a defect of collagen metabolism, based on elevated IH rates in patients with connective tissue disorders such as Ehlers-Danlos syndrome. Several authors reported that lower collagen I/III ratios were related to hernia-associated fascia, indicating immaturity and disorganization of healed fascial tissue. In our study, fascial collagen I/III protein ratios did not significantly differ between dHACM-treated fascia and healed, untreated fascia. This study tested fascia harvested on POD 28. Without wishing to be bound by theory, examination of fascial mechanics earlier in the healing process may have seen a more significant difference between the treatment arms. In previous studies, most observed hernias occurred by POD 7. For example, Xing et. al found that breaking strength in abdominal wall primed with human amnion-derived progenitor cells increased when compared to controls on POD 7, but not on POD 14 and 28. (Xing L, Franz M G, Marcelo C L, et al. "*Amnion-derived multipotent progenitor cells increase gain of incisional breaking strength and decrease incidence and severity of acute wound failure.*" J Burns Wounds. 2007; 7:e5) Other authors, however, have reported persistent increases in tensile strength at later post-operative times. (See, e.g., Tyrone J M, Marcus J R, Bonomo S R, et al. "*Transforming Growth Factor Beta 3 Promotes Fascial Wound Healing in a New Animal Model.*" Arch Surg. 2000; 135:1154-1159)

Example 9

To confirm broader applicability of PT graft material for the reduction of occurrence and development of IH, four additional PT graft material groups where studied using the rat model as described in Examples 7 & 8. The treatment groups comprised: Group A: cryopreserved umbilical cord and amniotic membrane matrix (Neox 100®, Amniox Medical Inc., Miami, FL.); Group B: tri-layer dehydrated placenta-derived tissue comprised of unseparated amniotic membrane and chorionic membrane with the intact intermediate layer (AmnioWrap$^{2}$™, Direct Biologics LLC, St. Louis, MO); Group C: cryopreserved umbilical cord and amniotic membrane (Neox Cord 1K®, Amniox Medical Inc., Miami, FL); and Group D: dehydrated trilayer amnion and chorion (NuShield®, Organogenesis Inc., Canton MA).

Results: The rate of IH occurrence in the rat model was significantly reduced compared to the 87.5% (n=8) (Example 7) observed in the control group, consistent with the 62.5% (n=8) reduction observed with dHACM sheets (Example 7). Specifically, 50% (n=8) IH occurrence was observed in Group A rats (cryopreserved umbilical cord and amniotic membrane matrix); 50% (n=6) IH occurrence was observed in Group B rats (tri-layer dehydrated placenta-derived tissue comprised of unseparated amniotic membrane and chorionic membrane with the intact intermediate layer); 50% (n=4) IH occurrence was observed in Group C rats (cryopreserved umbilical cord and amniotic membrane); and 57.1% (n=7) IH occurrence was observed in Group D rats (dehydrated trilayer amnion and chorion). IH development (size) was also significantly reduced in rats where IH occurred compared to the 14.4 mm±8.3 mm observed in controls (Example 7), significantly limiting size of hernia consistent with the 6.9 mm±6.0 mm observed with dHACM sheets (Example 7). Specifically, observed hernia sizes were as follows, Group A: 7.0 mm±2.7 mm; Group B: 8.7 mm±1.7 mm; Group C: 11.0 mm±2.7 mm; and Group D: 7.5 mm±2.1 mm. These findings evidence that implantation of all tested PT graft materials reduce IH formation at comparable rates, from 87.5% in controls to 50-60%. When IH did form, the average size was smaller in all PT groups, reducing hernias from 14.4 mm in controls to 6.9-8.7 mm for all PDTs except Neox 1K (average 11.0 mm).

Example 10

Examples 7 & 8 show that the tested PT dHACM sheets, significantly reduce IH occurrence and size development in an animal model in a manner consistent with other PT, as evidenced in Example 9. To validate extension of this finding to human subjects, a prospective cohort study of patients at high-risk for developing IH following abdominal surgery was performed.

Methods: In a multi-institutional quality improvement study, subjects undergoing abdominal surgery who were at high-risk for IH were prophylactically treated with onlay dHACM sheets following routine suture closure of their fascial incisions. No mesh was used. Preoperative risk factors were recorded. Subjects were followed for a minimum of 5 months for the development of IH. Expected number of IH was calculated using historical data.

Results: 8 subjects underwent 11 abdominal wall incisions. Incisions were grouped into high-risk (n=6) or extremely high-risk (n=5) based on preoperative risk factors (FIG. 4.). In our cohort, 1 IH developed (9.1%) in an extremely high-risk subject whose risk factors included advanced age, emergency surgery for perforated colon, and active smoking. The IH formed following a necrotizing infection that required abdominal wall debridement. The expected number of IH was 5.7 (51.4%), yielding a relative risk reduction 82.3%.

These data show that PT graft material including dHACM sheets reduce IH formation by 82.3% in high-risk patients.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

The singular forms "a", "an" and "the" include plural reference unless the context clearly dictates otherwise. The use of the word "a" or "an" when used in conjunction with the term "comprising" in the claims and/or the specification may mean "one," but it is also consistent with the meaning of "one or more," "at least one," and "one or more than one."

Wherever any of the phrases "for example," "such as," "including" and the like are used herein, the phrase "and without limitation" is understood to follow unless explicitly stated otherwise. Similarly "an example," "exemplary" and the like are understood to be nonlimiting.

The term "substantially" allows for deviations from the descriptor that do not negatively impact the intended purpose. Descriptive terms are understood to be modified by the term "substantially" even if the word "substantially" is not explicitly recited.

The terms "comprising" and "including" and "having" and "involving" (and similarly "comprises", "includes," "has," and "involves") and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a process involving steps a, b, and c" means that the process includes at least steps a, b and c. Wherever the terms "a" or "an" are used, "one or more" is understood, unless such interpretation is nonsensical in context.

As used herein the term "about" can refer to approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

This specification has been written with reference to various non-limiting and non-exhaustive embodiments. However, it will be recognized by persons having ordinary skill in the art that various substitutions, modifications, or combinations of any of the disclosed embodiments (or portions thereof) may be made within the scope of this specification. Thus, it is contemplated and understood that this specification supports additional embodiments not expressly set forth in this specification. Such embodiments may be obtained, for example, by combining, modifying, or reorganizing any of the disclosed steps, components, elements, features, aspects, characteristics, limitations, and the like, of the various non-limiting and non-exhaustive embodiments described in this specification.

Various elements described herein have been described as alternatives or alternative combinations, e.g., in a list of selectable actives, ingredients, or compositions. It is to be appreciated that embodiments may include one, more, or all of any such elements. Thus, this description includes embodiments of all such elements independently and embodiments including such elements in all combinations.

Any numerical range recited herein includes all values and ranges from the lower value to the upper value. For example, if a concentration range is stated as 1% to 50%, it is intended that values such as 2% to 40%, 10% to 30%, 1% to 3%, or 2%, 25%, 39% and the like, are expressly enumerated in this specification. These are only examples of what is specifically intended, and all possible combinations of numerical values and ranges between and including the lowest value and the highest value enumerated are to be considered to be expressly stated in this application. Numbers modified by the term "about" are intended to include+/-10% of the number modified.

The present disclosure may be embodied in other forms without departing from the spirit or essential attributes thereof and, accordingly, reference should be had to the following claims rather than the foregoing specification as indicating the scope of the invention. Further, the illustrations of arrangements described herein are intended to provide a general understanding of the various embodiments, and they are not intended to serve as a complete description. Many other arrangements will be apparent to those of skill in the art upon reviewing the above description. Other arrangements may be utilized and derived therefrom, such that logical substitutions and changes may be made without departing from the scope of this disclosure. Those skilled in the art will recognize, or be able to ascertain, using no more than routine experimentation, numerous equivalents to the specific substances and procedures described herein. Such equivalents are considered to be within the scope of this present disclosure, and are covered by the following claims.

What is claimed:

1. A method of reducing the occurrence and/or development of a hernia within a subject at risk of developing a hernia, comprising:
implanting a graft material in contact with an opening in an abdominal fascia in an abdominal wall, wherein the graft material is not affixed to the abdominal fascia, wherein the graft material promotes healing of the abdominal wall opening and wherein the graft material consists essentially of unseparated amniotic membrane and chorionic membrane with an intact intermediate layer therein.

2. The method of claim 1, wherein the unseparated amniotic membrane and chorionic membrane with an intact intermediate layer therein are a placenta-derived tissue, a placenta-derived membrane, or a combination thereof.

3. The method of claim 2, wherein the graft material further comprises umbilical cord vein, Wharton's jelly, or any combination thereof.

4. The method of claim 2, wherein the graft material consists of one or more layers of human unseparated amniotic membrane and chorionic membrane with an intact intermediate layer therein.

5. The method of claim 1, wherein the graft material consists of two or more layer of human unseparated amniotic membrane and chorionic membrane with an intact intermediate layer therein.

6. The method of claim 1, wherein the graft material consists of one or more layers of a dehydrated placental derived tissue, a decellularized placental derived tissue, a cross-linked placental derived tissue, a frozen placental derived tissue, a cryopreserved placental derived tissue, or a fresh placental derived tissue, or any combination thereof.

7. The method of claim 1, wherein the graft material consists of a sheet of unseparated amniotic membrane and chorionic membrane with an intact intermediate layer therein.

8. The method of claim 1, wherein implanting the graft material includes aligning the graft material with the opening in the abdominal wall.

9. The method of claim 1, wherein implanting the graft material comprises implanting the graft material over or ventral to the abdominal wall opening or implanting the graft material under or dorsal to the abdominal wall opening.

10. The method of claim 1, further comprising substantially or completely closing the abdominal wall opening prior to or after implanting the graft material.

11. The method of claim 1, wherein the opening comprises debrided fascia.

12. The method of claim 1, wherein the abdominal wall opening comprises a surgical incision.

13. The method of claim 12, wherein the surgical incision is caused by a surgery comprising laparotomy (celiotomy), laparoscopy, or stoma surgery.

14. A method of reducing occurrence of a hernia, comprising:

implanting a graft material in an abdominal fascia of a subject in contact with or in close proximity to an opening in the abdominal wall, wherein the graft material is placed as an overlay or an underlay without being affixed to the abdominal wall wherein the graft material consists of an unseparated amniotic membrane and chorionic membrane with an intact intermediate layer therein and reduces the occurrence of a hernia in the subject.

* * * * *